United States Patent
Fox

(10) Patent No.: US 12,285,483 B2
(45) Date of Patent: Apr. 29, 2025

(54) SOLANESOL VACCINE ADJUVANTS AND METHODS OF PREPARING SAME

(71) Applicant: ACCESS TO ADVANCED HEALTH INSTITUTE, Seattle, WA (US)

(72) Inventor: Christopher Bradford Fox, Sumner, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

(21) Appl. No.: 18/269,284

(22) PCT Filed: Oct. 16, 2021

(86) PCT No.: PCT/IB2021/059540
§ 371 (c)(1),
(2) Date: Jan. 2, 2024

(87) PCT Pub. No.: WO2022/136952
PCT Pub. Date: Jun. 30, 2022

(65) Prior Publication Data
US 2024/0050561 A1 Feb. 15, 2024

Related U.S. Application Data

(60) Provisional application No. 63/130,366, filed on Dec. 23, 2020.

(51) Int. Cl.
| | | |
|---|---|---|
| A61K 39/39 | (2006.01) | |
| A61K 9/10 | (2006.01) | |
| A61K 9/107 | (2006.01) | |
| A61K 39/145 | (2006.01) | |
| A61K 47/22 | (2006.01) | |
| A61P 37/04 | (2006.01) | |
| A61K 39/00 | (2006.01) | |

(52) U.S. Cl.
CPC ............ *A61K 39/39* (2013.01); *A61K 9/1075* (2013.01); *A61K 39/145* (2013.01); *A61K 47/22* (2013.01); *A61P 37/04* (2018.01); *A61K 2039/55566* (2013.01)

(58) Field of Classification Search
None
See application file for complete search history.

(56) References Cited

FOREIGN PATENT DOCUMENTS

WO     20071049790 A1     9/2007

OTHER PUBLICATIONS

Qin et al. mPEGylated solanesol micelles as redox-responsive nanocarriers with synergistic anticancer effect. Acta Biomaterialia 64 (2017) 211-222.*

Zhou et al. Microwave-assisted extraction of solanesol from tobacco leaves. Journal of Chromatography A, 1129 (2006) 135-139.*
Ru et al. In Vitro Antioxidant Properties of Flavonoids and Polysaccharides Extract from Tobacco (*Nicotiana tabacum* L.) Leaves. Molecules 2012, 17, 11281-11291.*
Ekapratiwi et al. The Effect of Tobacco Extracts based Biolarvicide Emulsion Formulation against Aedes aegypti Larvae. AIP Conf. Proc. 2092, 030009 (2019).*
Yan, et al., "Bioactivities and Medicinal Value of Solanesol and Its Accumulation, Extraction Technology, and Determination Methods," Biomolecules 2019, 9, 334; doi: 10.3390/biom9080334, 17 pages.
Wong, et al., "The immune correlates of protection for an avian influenza H5N1 vaccine in the ferret model using oil-in-water adjuvants," Scientific Reports Mar. 17, 20017; doi:10.1038/srep44727, 13 pages.
Qin, et al., "mPEGlyated solanesol micelles as redox-responsive nanocarriers with synergistic anticancer effect," Acta Materialla Inc., Sep. 27, 2017, di.org/10.1016/j.actbio.2017.09.040, 12 pages.
Yan, et al., "Solanesol: a review of its resources, derivatives, bioactivities, medicinal applications, and biosynthesis," Phytochem Rev. (2015) 14:403-417; doi 10.1007/s11101-015-9393-5, 15 pages.
International Search Report and Written Opinion for corresponding PCT Application PCT/IB2021/059540, dated Dec. 23, 2020, 9 pages.
Massaad-Massade, et al., "New Formulation for the Delivery of Oligonucleotides using "Clickable" siRNA-Polyisoprenoid-Conjugated Nanoparticles: Application to Cancers Harboring Fusion Oncogenes", Bioconjugate Chemistry, vol. 29, No. 6, Jun. 20, 2018, 8 pages.
Parodi, et al., "Inactivated Influenza Vaccines Recent Progress and Implications for the Elderly," Druge & Aging, vol. 28, No. 2., 2011, 2 pages.
Patel, et al., "Comparative Safety and Efficacy Profile of a Novel Oil in Water Vaccine Adjuvant Comprising Vitamins A and E and a Catechin in Protective Anti-Influenza Immunity," Nutrients, vol. 9, No. 5 (2017), 17 pages.
Office Action for related EPO Application No. 21 810 094.9-1111—mailed Jan. 4, 2024, 4 pages.
Office Action for related Canadian Application No. 3,173,408, mailed Jan. 26, 2024, 5 pages.
Qin, et al., PEGylated Solanesol for Oral Delivery of Coenzyme Q10, J Agric Food Chem. Apr. 26, 2017;65 (16)'3360-3367. doi: 10.1021/acs.jafc.7b001645, 8 pages.
Communication pursuant to Article 94(3) EPC for application No. 21810094.9 mailed Mar. 12, 2025, 4 pages.

* cited by examiner

*Primary Examiner* — Nianxiang Zou
(74) *Attorney, Agent, or Firm* — Benjamin Keim; Newport IP, LLC

(57) ABSTRACT

This disclosure describes the use of solanesol as an adjuvant in vaccine compositions, as well as related prophylactic and therapeutic methods. Solanesol may be used to replace squalene in vaccine compositions with similar or superior immunostimulatory effects. Solanesol, which is solid at room temperature, may be formulated for use in vaccine compositions by heating above its melting temperature in an aqueous solution to form a dispersion.

23 Claims, 19 Drawing Sheets

SOLANESOL VACCINE ADJUVANTS AND METHODS OF PREPARING SAME

CROSS REFERENCE TO RELATED APPLICATION

This application claims priority to U.S. Provisional Application No. 63/130,366 entitled "Solanesol Vaccine Adjuvants and Methods of Preparing Same," filed on Dec. 23, 2020, the disclosure of which is incorporated herein by reference in its entirety.

STATEMENT REGARDING FEDERALLY SPONSORED RESEARCH OR DEVELOPMENT

This invention was made with government support under R01AI1335673 awarded by the National Institute of Health. The government has certain rights in the invention.

FIELD

The present disclosure relates generally to the fields of pharmaceutical and vaccine formulations. More specifically, this disclosure describes the use of solanesol as an adjuvant in vaccine compositions, as well as related prophylactic and therapeutic methods.

BACKGROUND

The goal of immunization is to generate specific and strong immune responses against target antigens with minimal side effects. However, some vaccines require adjuvants to enhance the strength and duration of the immune response to the target antigens. Adjuvants help stimulate protective immunity based on antibodies and effector T cell functions. Most, if not all, adjuvants enhance T and B cell responses by engaging components of the innate immune system. Adjuvants can also minimize the antigen dose necessary to confer immunity. Aluminum salts were some of the first substances used as adjuvants. Currently, squalene emulsions are among the most widely employed vaccine adjuvant formulations.

Squalene is a naturally occurring oligoisoprene (i.e., a very low molecular weight polymer of isoprene) that is liquid at room temperature. Squalene is primarily derived from shark liver, a source with sustainability concerns. Although squalene is also available from plant sources, extraction is more challenging. Global pandemics may create the need for billions of vaccine doses to be manufactured quickly. Inability to obtain sufficient quantities of adjuvants such as squalene could constrain vaccine production capacity.

New compounds that can be used as adjuvants, particularly compounds with strong immune-stimulating properties that are available from sustainable plant-based sources, are desirable for vaccine development. The following disclosure is made with respect to these and other considerations.

SUMMARY

This disclosure describes the use of solanesol as an adjuvant in immunostimulatory compositions such as oil-in-water vaccines. This disclosure also provides a method for generating pharmaceutical compositions such as vaccine compositions that include solanesol.

Solanesol is a long-chain polyisoprenoid alcohol compound with nine isoprene units available from plant sources that has not been previously used as a vaccine adjuvant. Unlike other metabolizable oils commonly used in vaccines, such as squalene, solanesol is solid at room temperature. Thus, formulation techniques used for squalene and other oils are not readily adaptable to use with solanesol.

The inventors of this application have discovered solanesol can be put into a pharmaceutical composition by melting the solanesol and generating an emulsion while maintaining the composition at an elevated temperature. Surprisingly, vaccines created in this manner with solanesol were found to induce responses similar to vaccines that use squalene as a metabolizable oil. The vaccines were additionally found to have similar stability as compared to vaccines that use squalene.

An immunostimulatory composition that includes solanesol as an adjuvant may also include one or more of a surfactant, a tonicity agent, and an antioxidant. A vaccine composition additionally includes an antigen. The antigen may be any antigenic compound such as a polypeptide, a nucleic acid encoding a polypeptide, or a pathogen. The surfactant may be a hydrophilic surfactant, a hydrophobic surfactant, or both. In an implementation, the hydrophilic surfactant is polyoxyethylene-polyoxypropylene block copolymer (pluronic F68). In an implementation, the hydrophobic surfactant is 1,2-dimyristoyl-sn-glycero-3-phosphocholine (DMPC) or a copolymer of polyoxyethylene and polyoxypropylene (poloxamer 188). The antioxidant may be alpha-tocopherol (vitamin E). The tonicity agent may be glycerol.

Immunostimulatory compositions that include solanesol may be created by melting solid solanesol in a buffered aqueous solution heated above the melting point of solanesol. The buffered aqueous solution may be a phosphate buffer that may contain glycerol and a surfactant. Solid solanesol is added to the buffered aqueous solution and allowed to dissolve. This creates an oil phase that contains liquid solanesol. One or more surfactants may also be added to the buffered aqueous solution. A dispersion is formed by homogenization of the heated solution. The dispersion may be microfluidized while maintaining a temperature above the melting point of solanesol. The particle size of the dispersed solanesol may be reduced to about 100 nm or less while the temperature is maintained above the melting point of solanesol. An antioxidant may be added to the oil phase of the dispersion.

It is to be understood that one, some, or all of the properties of the various implementations described herein may be combined to form other implementations consistent with the present disclosure. These and other aspects of the present disclosure will become apparent upon reference to the following detailed description and attached drawings. All references disclosed herein are hereby incorporated by reference in their entirety as if each were incorporated individually.

DETAILED DESCRIPTION

Figure 1:
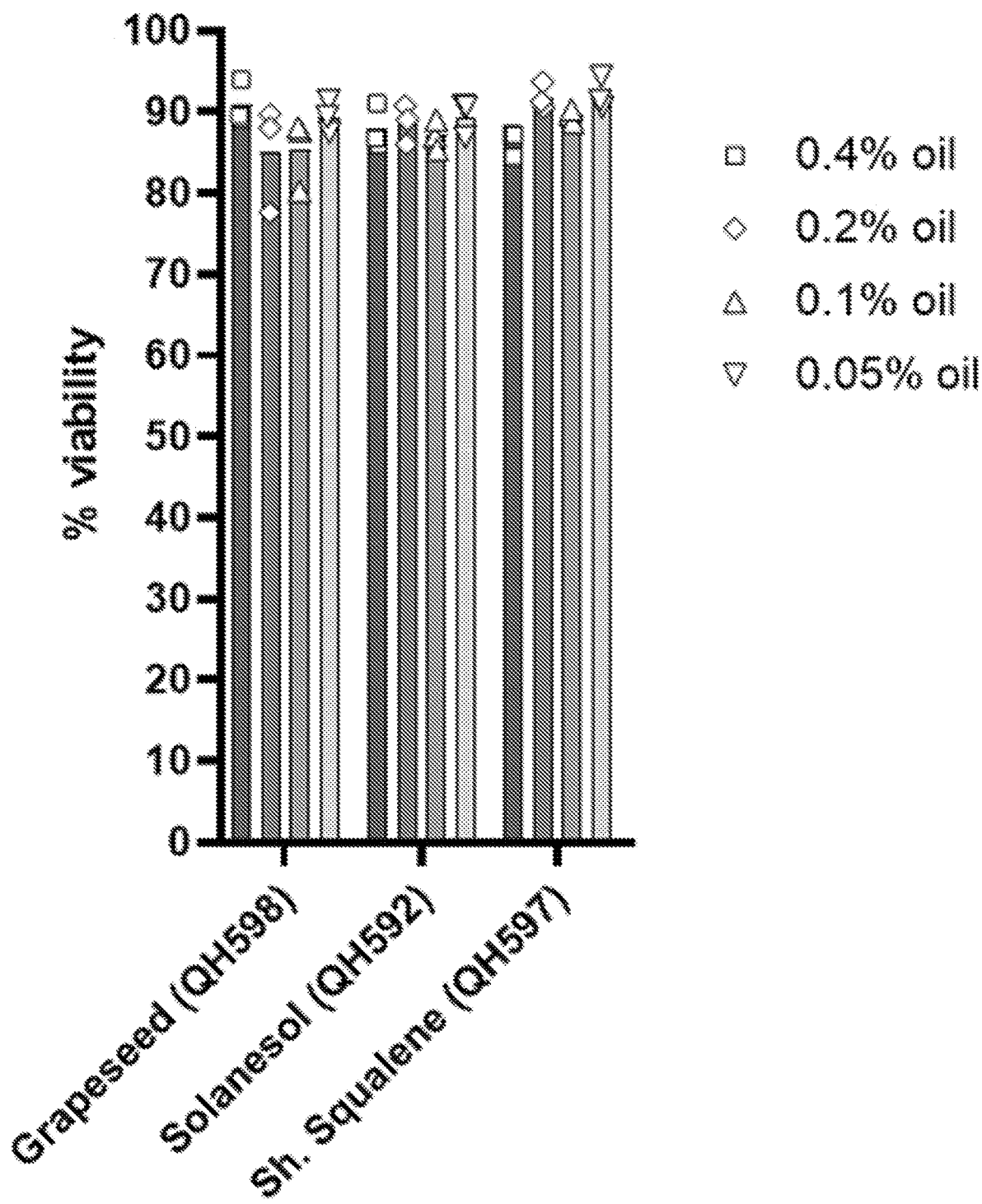
FIG. 1 shows the percentage of viable PBMC after incubation with one of three different vaccine compositions at one of four different oil concentrations. The bar height is the average of values from 3 different samples. The PBMC maintained viability across all vaccine formulations and oil concentrations.

Solanesol is a noncyclic terpene alcohol comprised of nine isoprene units with 45 carbon atoms. Pure solanesol is a waxy white solid at room temperature that is insoluble in water. Solanesol is extracted from plants, particularly tobacco leaves but is also found in other solanaceous crops, including potatoes, tomatoes, eggplants, and peppers. Solanesol is used in the pharmaceutical industry as an intermediate for the synthesis of ubiquinone drugs, such as coenzyme Q10 and vitamin K2. Solanesol possesses antibacterial, antifungal, antiviral, anticancer, anti-inflammatory, and anti-ulcer activities. Solanesol derivative micelles have been used in the delivery of hydrophobic drugs. The structure of solanesol is shown below.

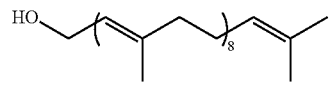

Of course, it will be understood that the immunostimulatory compositions can be used in the presence of one or more antigens to elicit antigen-specific immune responses. Alternatively, the immunostimulatory compositions can be used in the absence of antigen to elicit a non-specific immune response.

General Techniques

The practice of the present disclosure will employ, unless otherwise indicated, conventional techniques of molecular biology, recombinant DNA, biochemistry, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); MuUis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Maryland (1989).

Definitions

The following terms have the following meanings unless otherwise indicated. Any undefined terms have their art recognized meanings.

In the present description, the terms "about" and "consisting essentially of mean±20% of the indicated range, value, or structure, unless otherwise indicated.

The use of the alternative (e.g., "or") should be understood to mean either one, both, or any combination thereof of the alternatives.

As used herein, the terms "include," "have" and "comprise" are used synonymously, which terms and variants thereof are intended to be construed as non-limiting.

As used herein and in the appended claims, the singular forms "a," "an," and "the" include plural reference unless the context clearly indicates otherwise.

An "individual" or a "subject" is any mammal. Mammals include, but are not limited to humans, primates, farm animals, sport animals, pets (such as cats, dogs, horses), and rodents.

Vitamin E refers to both tocopherols (TCPs) and tocotrienols and can be naturally occurring or synthetic.

Ambient temperature is between 15° C. and 25° C.

A "polynucleotide" or "nucleic acid," as used interchangeably herein, refer to polymers of nucleotides of any length, include DNA and RNA. The nucleotides can be, for example, deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

Dispersions

A dispersion is a system in which distributed particles of one material are dispersed in a continuous phase of another material. Dispersions do not display any structure; i.e., the particles (or in case of emulsions: droplets) dispersed in the liquid or solid matrix (the "dispersion medium") are assumed to be statistically distributed. Dispersion is a process by which (in the case of solid dispersing in a liquid) agglomerated particles are separated from each other, and a new interface between the inner surface of the liquid dispersion medium and the surface of the dispersed particles is generated. When discussing suspensions of solid particles in liquid media, the zeta potential is most often used to quantify the degree of dispersion, with suspensions possessing a high absolute value of zeta potential being considered as well-dispersed. A solution describes a homogeneous mixture where the dispersed particles will not settle if the solution is left undisturbed for a prolonged period of time.

Aqueous Phase

The aqueous phase of the composition is typically a buffered salt solution (e.g., saline) or water. The buffered salt solution may be an aqueous solution that comprises a salt (e.g., NaCl), a buffer (e.g., a citrate buffer), and can further comprise, for example, an osmolality adjusting agent (e.g., a saccharide), a polymer, a surfactant, or a combination thereof. If the emulsions are formulated for parenteral administration, it is preferable to make up final buffered solutions so that the tonicity, i.e., osmolality is essentially the same as normal physiological fluids to prevent undesired post-administration consequences, such as post-administration swelling or rapid absorption of the composition. It is also preferable to buffer the aqueous phase to maintain a pH compatible with normal physiological conditions. Also, in certain instances, it may be desirable to maintain the pH at a particular level to ensure the stability of certain components of the composition. For example, it may be desirable to prepare a composition that is isotonic (i.e., the same permeable solute (e.g., salt) concentration as the normal cells of the body and the blood) and isosmotic. To control tonicity, the composition may comprise a physiological salt, such as a sodium salt. In some aspects, sodium chloride (NaCl), for example, may be used at about 0.9% (w/v) (physiological saline). Other salts that may be present include, for example, potassium chloride, potassium dihydrogen phosphate, disodium phosphate, magnesium chloride, calcium chloride, and the like. Non-ionic tonicifying agents can also be used to control tonicity. Monosaccharides classified as aldoses such as glucose, mannose, arabinose, and ribose, as well as those classified as ketoses such as fructose, sorbose, and xylulose can be used as non-ionic tonicifying agents in the present disclosure. Disaccharides such as sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents that can be useful in the present disclosure. Non-ionic tonicity modifying agents can be present, for example, at a concentration of from about 0.10% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 4.0-8.0 or from about 4.5 to about 6.8. In one implementation, the aqueous phase is, or the buffer prepared using, RNase-free water or DEPC treated water. In some cases, high salt in the buffer might interfere with the complexation of negatively charged molecules to the emulsion particle therefore is avoided. In other cases, a certain amount of salt in the buffer may be included.

In one implementation, the buffer is 10 mM citrate buffer (e.g., sodium citrate) with a pH between about 5.0 and 8.0. In another implementation, the aqueous phase is, or the buffer is prepared using, RNase-free water or DEPC treated water. In other implementations, the compositions of the present disclosure do not comprise a citrate buffer.

The aqueous phase may also comprise additional components such as molecules that change the osmolarity of the aqueous phase or molecules that stabilize the negatively charged molecule after complexation. Preferably, the osmolarity of the aqueous phase is adjusting using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.), or combinations thereof. If desired, a nonionic polymer (e.g., a poly(alkyl glycol) such as polyethylene glycol, polypropylene glycol, or polybutlyene glycol) or nonionic surfactant can be used.

Surfactant

Surfactants, or surface-active agents, are compounds that lower the surface tension between two liquids or between a liquid and a solid. Surfactants are amphiphilic, meaning that they contain hydrophilic (water-loving) head groups and hydrophobic (water-hating, or oil-loving) tails. Surfactants adsorb at the interface between oil and water, thereby decreasing the surface tension. An emulsifier is a surfactant that stabilizes emulsions. Emulsifiers coat droplets within an emulsion and prevent them from coming together, or coalescing.

In some implementations, the compositions of the present disclosure comprise a surfactant. The surfactant may be a hydrophilic surfactant. A hydrophilic surfactant may have an HLB value of about 10-30, 10-15, 10-20, 10-25, 15-20, 15-25, 15-30, 20-25, 20-30, 10, 11, 12, 13, 14, 15, 16, 17, 18, 19, 20, 21, 22, 23, 24, 25, 26, 27, 28, 29 or 30. In some implementations, the hydrophilic surfactant is pluronic F68 (HLB 29). The surfactant may be a hydrophobic surfactant. The hydrophobic surfactant may have an HLB value of about 1-6, 2-5, 1-4, 3-6, 1, 2, 3, 4, 5, or 6. In some implementations, the hydrophobic surfactant is a phospholipid. Compositions of the present disclosure may include both hydrophobic surfactants and hydrophilic surfactants.

There are a number of surfactants specifically designed for and commonly used in biological applications. Surfactants useful for implementations of this disclosure include Pluronic F68, Tween 80, polysorbate 80 (CAPMUL POE-0 low PV surfactant, ABITEC Corp., Janesville, Wis.), polyethylene 660 12-hydroxystearate (SOLUTOL HS15, BASF Corp., Chicago, Ill.), poloxamer 188 (PLURONIC Q F68 block co-polymer, BASF Corp., Chicago, Ill.), sodium cholate, glycerodeoxy cholate, and phosphatidyl choline. Other suitable surfactants include sphingolipids such as sphingomyelin and sphingosine and phospholipids such as egg phosphatidylcholine, 1,2-Dimyristoyl-sn-glycero-3-phosphoethanolamine, L-a-Phosphatidylethanolamine, and 1,2-Dipalmitoyl-sn-glycero-3-phosphocholine (DPPC) or mixtures thereof. DPPC is acceptable for use in humans. In some implementations, the surfactant is DMPC, DOPC, and/or POPC (including synthetic DMPC, DOPC, and POPC). Brij surfactants may be used. (Maria E. N. P. Ribeiro, Carolina L. de Moura, Mariano G. S. Vieira, Nilce V. Gramosa, Chiraphon Chaibundit, Marcos C. de Mattos, David Attwood, Stephen G. Yeates, S. Keith Nixon, Nigila M. P. S. Ricardo, Solubilisation capacity of Brij surfactants, International Journal of Pharmaceutics, Volume 436, Issues 1-2, 2012, Pages 631-635, ISSN 0378-5173, doi.org/10.1016/j.ijpharm.2012.07.032.) One or more surfactants may be used.

Additional examples of suitable surfactants are described in WO2005009462A2.

In some implementations, the surfactant is present at a ratio of about 100:1 (oil:surfactant). In some implementations, the surfactant is present at a concentration of about 0.018% w/v. In some implementations, the surfactant is present at a concentration of about 0.0001% w/v, about 0.0005% w/v, about 0.001% w/v, about 0.005% w/v, about 0.01% w/v, about 0.011% w/v, about 0.012% w/v, about 0.013% w/v, about 0.014% w/v, about 0.015% w/v, about 0.016% w/v, about 0.017% w/v, about 0.018% w/v, about 0.019% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v. The percentages and ratios described herein refer to the ratios and percentages in either the oil-in-water emulsion formulation prior to lyophilization or in the oil-in-water emulsion upon reconstitution.

Hydrophilic-Lipophilic Balance (HLB)

The hydrophilic-lipophilic balance (HLB) of an emulsion allows for the estimation of the hydrophilic or lipophilic force of a surfactant. The HLB of an amphiphilic molecule is generally calculated as follows: HLB=(20×Weight of the hydrophilic part)/(Weight of the amphiphilic molecule). Methods for determining the HLB of an emulsion are known in the art. See, e.g., world wide web at firp.ula.ve/archivos/historicos/76_Book_HLB_ICI.pdf and at chemistscorner.com/hlb-the-easiest-way-to-create-an-emulsion/.

The HLB may have a value ranging from 0 (for the most lipophilic molecule) to 20 (for the most hydrophilic molecule). According to the chemical composition of the surfactant (notably for example the addition of ethoxyl groups or of alkene oxides), this estimation may change and the domain of HLB value may increase (for example, the LUTROL F68® has a HLB of 29). With a mixture of surfactants, the HLB of the mixture is the addition of the HLB of each surfactant, balanced by its Weight ratio: HLB=(HLB surfactant X×Weight surfactant X)+(HLB surfactant Y×Weight surfactant Y)/(Weight surfactant X+Weight surfactant Y).

The specific surfactants and ratio of a hydrophilic surfactant to a hydrophobic surfactant may be selected to achieve an overall HLB value. An emulsion may have a final HLB from about 9 to about 12, from about 9.5 to about 11.5, and from about 10 to about 11.5. In some implementations, the HLB of the emulsion is from about 10.5 to about 11.0. In some implementations, the hydrophobic:lipophilic balance (HLB) of the oil-in-water emulsion is greater than about 9, or greater than about 10, or between about 9-12.

Tonicity Agent

In an implementation, the vaccine compositions may include a tonicity agent. A tonicity agent functions to render a solution similar in osmotic characteristics to physiologic fluids. Examples of tonicity agents include dextrose, mannitol, sodium chloride, potassium chloride, and glycerin. A vaccine composition formulated with a tonicity agent will have essentially the same osmotic pressure as human blood. Isotonic or physiologic formulations will generally have an osmotic pressure from about 275-325 mOsm. Slightly hypotonic pressure is 250-270 and slightly hypertonic pressure is 330-350 mOsm. Osmotic pressure can be measured, for example, using a vapor pressure or freezing point depression type osmometer. Typically, particular excipients referred to in the field as "tonicity modifiers" or "tonicity agents" are used to control the tonicity of a pharmaceutical formulation. Salts (NaCl, KCl, $MgCl_2$, $CaCl_2$), etc.) represent commonly used as tonicity modifiers. In addition, excipients such as, but not limited to sucrose, mannitol, trehalose, glycine, etc. can function as tonicity modifiers. In any of the implementations described herein, the tonicity agent can be, for example, a polyol such as mannitol or glycerol. Agents that can be added to the subject disclosure to make the immunostimulatory composition isotonic include dextrose, glycerol, mannitol, sorbitol, PEG 300, PEG 400, and polyethylene glycol.

Antioxidant

In implementations, the immunostimulatory compositions comprise an antioxidant. Illustrative antioxidants useful in the emulsion of the subject disclosure include, but are not limited to, alpha-tocopherol (vitamin E), sodium bisulfite, and ascorbic acid.

Stability

The stability of the vaccine compositions provided herein is assessed following storage by the aid of one or more assays, for example, biophysical and biochemical assays. Stability may be assessed by measuring the change in particle size during storage. Particle size stability may be evaluated by measuring average particle size before and after storage. Vaccine compositions may be stored at about 3° C., 4° C., 5° C., 6° C., 7° C., 8° C., 9° C., or 10° C.

For example, dynamic light scattering (DLS) can be used to evaluate emulsion particle size. In some implementations, this is compared to the emulsion particle size prior to storage. In some implementations, the emulsion particle size is not compared to the particles size prior to storage. In some implementations herein, the particle size is determined by measuring the Z-average diameter (Z-avg) of the vaccine composition. In particular implementations, a stable composition is indicated when a Z-average diameter of particle size increases by less than 20% from initial size In some implementations, dynamic light scattering (DLS) can be used to evaluate the PdI. In some implementations, this is compared to the PDI of the vaccine composition prior to storage.

In one embodiment, the zeta potential is evaluated following storage. For example, dynamic light scattering (DLS) can be used to evaluate the zeta potential. In some implementations, this is compared to the zeta potential prior to storage.

Therapeutics

In some implementations, the composition is useful for therapeutic purposes. Thus, in some implementations, the compositions described comprise a bioactive agent for the treatment of a disease, condition, or disorder.

In some implementations, the agent is useful for the treatment or prevention of allergy, cancer, infectious disease, autoimmunity, or addiction. In some implementations, the agent is useful for the stimulating, enhancing, and/or modulating an immune response.

In some aspects of the disclosed implementations, the compositions comprise cancer antigens or nucleic acids encoding a cancer antigen. In some implementations, a vaccine composition that comprises a cancer antigen will be useful against any cancer characterized by tumor-associated antigen expression, such as HER-2/neu expression or other cancer-specific or cancer-associated antigens.

Compositions and methods according to certain implementations of the present disclosure may also be used for the prophylaxis or therapy of autoimmune diseases, which include diseases, conditions or disorders wherein a host's or subject's immune system detrimentally mediates an immune response that is directed against "self tissues," cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

The compositions of the present disclosure may include antigens associated with respiratory diseases, such as those caused or exacerbated by bacterial infection (e.g. pneumococcal), for the prophylaxis and therapy of conditions such as chronic obstructive pulmonary disease (COPD).

In some implementations, the compositions of the present disclosure are used to boost or enhance an immune response in a subject. In some such implementations, the bioactive agent is an adjuvant. Nonlimiting adjuvants include TLR agonists (including TLR2, TLR3, TLR4, TLR7, TLR8, and TLR9 agonists), Rig-I agonists, saponins, carbohydrates, carbohydrate polymers, conjugated carbohydrates, whole viral particles, virus-like particles, viral fragments, and cellular fragments. Examples of such adjuvants include, but are not limited to, double-stranded RNA, RIBOXXOL, poly(I:C), and Hiltonol®.

In some aspects, the compositions of the present disclosure are useful for enhancing or eliciting an immune response in a host, a patient, or in cell culture. As used herein, the term "subject" refers to any mammal. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells, and dendritic cells). Such cells may be isolated by any of a variety of techniques well known to those of ordinary skill in the art (e.g., Ficoll-hypaque density centrifugation). The cells may (but need not) have been isolated from a patient afflicted with cancer and may be reintroduced into a patient after treatment.

Immune responses may often be regarded, for instance, as discrimination between self and non-self structures by the cells and tissues of a host's immune system at the molecular and cellular levels, but the disclosure should not be so limited. For example, immune responses may also include immune system state changes that result from immune recognition of self molecules, cells, or tissues, as may accompany any number of normal conditions such as typical regulation of immune system components, or as may be present in pathological conditions such as the inappropriate autoimmune responses observed in autoimmune and degenerative diseases. As another example, in addition to induction by upregulation of particular immune system activities (such as antibody and/or cytokine production, or activation of cell-mediated immunity) immune responses may also include suppression, attenuation, or any other down-regulation of detectable immunity, which may be the consequence of the antigen selected, the route of antigen administration, specific tolerance induction or other factors.

Determination of the induction of an immune response by the vaccines of the present disclosure may be established by any of a number of well-known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptides, carbohydrate, nucleotide, and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, MA; Mishell and Shigii (eds.) Selected Methods in Cellular Immunology, 1979 Freeman Publishing, San Francisco, CA; Green and Reed, 1998 Science 281: 1309 and references cited therein).

Detection of antigen-specific antibody production may be achieved, for example, by assaying a sample (e.g., an immunoglobulin containing a sample such as serum, plasma, or blood) from a host treated with a vaccine according to the present disclosure using in vitro methodologies such as radioimmunoassay (RIA), enzyme linked immunosorbent assays (ELISA), equilibrium dialysis or solid phase immunoblotting including Western blotting. In some implementations ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus, and reagents that are readily available from commercial sources (e.g., Sigma, St. Louis, MO; see also R & D Systems 2006 Catalog, R & D Systems, Minneapolis, MN).

Vaccine Composition

In some implementations, a vaccine composition or vaccine formulation is used to elicit or enhance the immunoreactivity or an immune response in a host to an antigen. In certain implementations, the compositions described herein (e.g., a vaccine composition) comprise an antigen or antigenic composition capable of eliciting an immune response against a human or other mammalian pathogen.

The present disclosure thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells, or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example, cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Determination of the induction of an immune response by the compositions of the present disclosure may be established by any of a number of well-known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example, cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, MA; Mishell and Shigii (eds.) Selected Methods in Cellular Immunology, 1979 Freeman Publishing, San Francisco, CA; Green and Reed, 1998 Science 281:1309 and references cited therein).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma, or blood) from a host treated with a vaccine according to the present disclosure using in vitro methodologies such as radioimmunoassay (RIA), enzyme linked immunosorbent assays (ELISA), equilibrium dialysis or solid phase immunoblotting including Western blotting. In implementations ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus, and reagents that are readily available from commercial sources (e.g., Sigma, St. Louis, MO; see also R & D Systems 2006 Catalog, R & D Systems, Minneapolis, MN).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well-established marker antigen systems, immunohistochemistry, or other relevant assays. These and other assays may be found, for example, in Rose et al. (Eds.), Manual of Clinical Laboratory Immunology, 5th Ed., 1997 American Society of Microbiology, Washington, DC.

Accordingly, it is contemplated that the compositions provided herein will be capable of eliciting or enhancing in a host at least one immune response that is selected from a Th1-type T lymphocyte response, a TH2-type T lymphocyte response, a cytotoxic T lymphocyte (CTL) response, an antibody response, a cytokine response, a lymphokine response, a chemokine response, and an inflammatory response. In certain implementations the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, CCL2, CCL4, CCL5, CXCL1, and CXCL5, and a lymphocyte response that is selected from a memory T cell response, a memory B cell response, an effector T cell response, a cytotoxic T cell response and an effector B cell response.

Pharmaceutical Composition

Provided herein are pharmaceutical compositions comprising dispersions or emulsions or nanostructured lipid carriers as described herein. In some implementations, the composition further comprises a pharmaceutically acceptable carrier, excipient, or diluent. Illustrative carriers will be nontoxic to recipients at the dosages and concentrations employed. "Pharmaceutically acceptable carriers" for therapeutic use are well known in the pharmaceutical art and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives. Id at 1449. In addition, antioxidants and suspending agents may be used. Id.

In some implementations provided herein, the pharmaceutical compositions provided herein are capable of being filtered through a 0.45 micron filter. In some implementations, the pharmaceutical composition is capable of being filtered through a 0.20 micron filter. In some implementations, the pharmaceutical composition is capable of being filtered through a 0.22 micron filter.

"Pharmaceutically acceptable salt" refers to salts of the compounds of the present disclosure derived from the combination of such compounds and an organic or inorganic acid (acid addition salts) or an organic or inorganic base (base addition salts). The compositions of the present disclosure may be used in either the free base or salt forms, with both forms being considered as being within the scope of the present disclosure.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033,598; 7,018,345; 6,970,739), sonophoretic (e.g., U.S. Pat. Nos. 4,780,212; 4,767,402; 4,948,587; 5,618,275; 5,656,016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral, intratumoral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the disclosure in aerosol form may hold a plurality of dosage units.

The term "effective amount" or "therapeutically effective amount" refers to an amount that is sufficient to achieve or at least partially achieve the desired effect, e.g., sufficient to generate the desired immune response. An effective amount of a composition is administered in an "effective regime." The term "effective regime" refers to a combination of the amount of the composition being administered and dosage frequency adequate to accomplish the desired effect.

Actual dosage levels may be varied so as to obtain an amount that is effective to achieve a desired response for a particular patient, composition, and mode of administration, without being toxic to the patient. The selected dosage level will depend upon a variety of pharmacokinetic factors in combination with the particular compositions employed, the age, sex, weight, condition, general health and prior medical history of the subject being treated, and like factors well-known in the medical arts.

In therapeutic implementations provided herein, a dosage of about 1 μg/kg to about 10 mg/kg of a therapeutic pharmaceutical composition is administered. It will be evident to those skilled in the art that the number and frequency of administrations will be dependent upon the response of the subject.

In vaccine-based implementations provided herein, about 1 μg-100 μg of the antigen or 0.1 μg-10 mg of the nucleic acid encoding the antigen will be administered per administration. formulations of the present permit a human dose of from about 0.1 ug, about 1 ug, about 5 μg, or about 10 μg to about 500 μg of replicon RNA. formulations of the present permit a human dose of about 5 μg to about 20 ug replicon RNA.

It will be evident to those skilled in the art that the number and frequency of administrations will be dependent upon the response of the subject. formulations allow for therapeutic efficacy after as little as one immunization.

For oral administration, an excipient and/or binder may be present. Examples are sucrose, kaolin, glycerin, starch dextrins, sodium alginate, carboxymethylcellulose, and ethyl cellulose. Coloring and/or flavoring agents may be present. A coating shell may be employed.

The composition may be in the form of a liquid, e.g., an elixir, syrup, solution, emulsion, or suspension. The liquid may be for oral administration or for delivery by injection, as two examples. When intended for oral administration, compositions may contain one or more of a sweetening agent, preservatives, dye/colorant, and flavor enhancer. In a composition intended to be administered by injection, one or more of a surfactant, preservative, wetting agent, dispersing agent, suspending agent, buffer, stabilizer, and isotonic agent may be included.

A liquid pharmaceutical composition as used herein, whether in the form of a solution, suspension, or other like form, may include one or more of the following carriers or excipients: sterile diluents such as water for injection, saline solution, physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes, or multiple dose vials made of glass or plastic. An injectable pharmaceutical composition is preferably sterile.

The pharmaceutical composition may be in the form of a lyophilized cake. In some implementations, the cake referred to herein is a porous and spongy structure-like material resulting from the lyophilization process; or the cake is the solid content remaining after the freeze-drying process. In some implementations, the cake's appearance can be described as a spongiform cake, lovely cake, and elegant cake. In some implementations, if no cake forms upon lyophilization, the resulting composition can be characterized as a clear film, a thin film, a thick white film, or solidified bubbles. Desired cakes refer to cakes that after exposure, storage, or maintenance of the cake at temperatures described above the typical cold chain storage of 2-8° C., or above or at about 8° C. display desired characteristics of a lyophilized vaccine formulation. ("Excipients used in lyophilization of small molecules" Ankit Bahetia, Lokesh Kumarb, Arvind K. Bansal, J. Excipients and Food Chem. 1 (1) 2010; 41-54.)

When lyophilized, the pharmaceutical composition may comprise one or more lyophilization excipients. Lyophilization excipients, as used herein, may refer to substances other than the pharmacologically active drug which are included in the lyophilization process to contribute to the form or formulation of a suitable cake structure. Lyophilization excipients may include bulking agents, buffering agents, or solubilizing agents.

In some implementations, lyophilization is performed using a VirTis (Gardiner, NY) Advantage 2.0 EL-85 benchtop freeze dryer. The lyophilization recipe can use a thermal treatment schedule including a 10-hour freezing step from 4 to −40° C., and an annealing step at −15° C. The primary drying phase (at 100 mTorr) may last from 18.3 hours from −40° C. to 25° C. Finally, a secondary drying phase at 50 mTorr can be employed at 25° C. for 9 hours.

Antigens

In some implementations, the formulations of the disclosure will also comprise one or more antigens.

In some implementations, the antigen is an influenza-related antigen. In some implementations, the antigen is an influenza-causing antigen. In some implementations, the antigen is from an influenza causing virus. In one embodiment, the antigen comprises H5N1. In one embodiment, the antigen comprises H5N1.

An antigen, for use in certain implementations of the herein described vaccine compositions and methods employing GLA, may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain implementations the antigen may be, or may be derived from, or may be immunologically cross-reactive with, an infectious pathogen and/or an epitope, biomolecule, cell, or tissue that is associated with infection, cancer, autoimmune disease, allergy, asthma, or any other condition where stimulation of an antigen-specific immune response would be desirable or beneficial.

Certain implementations the vaccine formulations of the present disclosure contain an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gpl, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus), Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

In certain implementations, the vaccine formulations of the present disclosure contain an antigen for Severe Acute Respirator Syndrome Coronavirus 2 (SARS-CoV-2). In some implementations, the payload is a polypeptide antigen specific for Severe Acute Respiratory Syndrome Coronavirus 2 (SARS-CoV-2). SARS-CoV-2 includes the major structural proteins spike (S), envelope (E), membrane (M), and nucleocapsid (N). In some implementations, the payload is selected from the group consisting of the SARS-CoV-2 S, E, M, and N proteins and fragments thereof.

In certain other implementations the vaccine formulations of the present disclosure contains an antigen or antigenic composition capable of eliciting an immune response against a human or other mammalian pathogen, which antigen or antigenic composition may include a composition derived from one or more bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, —B or —C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *Clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including E. equi and the agent of the Human Granulocytic Ehrlichiosis; *Rickettsia* spp., including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including L. interrogans; *Treponema* spp., including *T. pallidum* (for example the rare outer membrane proteins), *T. denticola, T. hyodysenteriae*; or other bacterial pathogens.

In certain other implementations the vaccine formulations of the present disclosure contain an antigen or antigenic composition capable of eliciting an immune response against a human or other mammalian pathogen, which antigen or antigenic composition may include a composition derived from one or more parasites (See, e.g., John, D. T. and Petri, W. A., Markell and Voge's Medical Parasitology-^ Ed., 2006, WB Saunders, Philadelphia; Bowman, D. D., Georgis' Parasitology for Veterinarians—8th Ed., 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis,* and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain implementations may therefore contemplate vaccine compositions that include an antigen derived from *Schisostoma* spp., *Schistosoma mansonii, Schistosoma haematobium*, and/or *Schistosoma japonicum*, or derived from yeast such as *Candida* spp., including *C. albicans; Cryptococcus* spp., including *C. neoformans*.

According to certain other implementations as disclosed herein, the vaccine compositions and related formulations and methods of use may include an antigen that is derived from a cancer cell, as may be useful for the immunotherapeutic treatment of cancers. For example, the adjuvant formulation may find utility with tumor rejection antigens such as those for prostate, breast, colorectal, lung, pancreatic, renal, or melanoma cancers. cancer or cancer cell-derived antigens include MAGE 1, 3, and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 Current Opinions in Immunology 8, pps 628-636; Van den Eynde et al., International Journal of Clinical & Laboratory Research (1997 & 1998); Correale et al. (1997), Journal of the National Cancer Institute 89, p. 293. These non-limiting examples of cancer antigens are expressed in a wide range of tumor types such as melanoma, lung carcinoma, sarcoma, and bladder carcinoma. See, e.g., U.S. Pat. No. 6,544,518.

Other tumor-specific antigens are suitable for use with a vaccine composition according to certain presently disclosed implementations include, but are not restricted to, tumor-specific or tumor-associated gangliosides such as $GM_2$, and $GM_3$ or conjugates thereof to carrier proteins; or an antigen for use in a vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., Proc. Nat. Acad. Sci. USA 95(4) 1735-1740 1998), PSMA or, in a one embodiment an antigen known as Prostase. (e.g., Nelson, et al., Proc. Natl. Acad. Sci. USA (1999) 96: 3114-3119; Ferguson, et al. Proc. Natl. Acad. Sci. USA 1999. 96, 3114-3119; WO 98/12302; U.S. Pat. No. 5,955, 306; WO 98/20117; U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present disclosure include: Plu-1 (J Biol. Chem 21 (22) 15633-15645, 1999), HASH-1, HasH-2, Cripto (Salomon et al Bioessays 199, 21:61-70, U.S. Pat. No. 5,654,140) and Criptin (U.S. Pat. No. 5,981,215).

Additionally, antigens particularly relevant for vaccines in the therapy of cancer also comprise tyrosinase and survivin.

In other implementations, the antigen or antigens used in the compositions of the disclosure include antigens associated with respiratory diseases, such as those caused or exacerbated by bacterial infection (e.g., pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g., pneumococcal) infection (Clin Microbiol Rev. 2001 April; 14(2):336-63).

Nucleic Acids

Certain implementations of the vaccine formulations of the present disclosure comprise a nucleic acid molecule (e.g., DNA or RNA) that encodes an antigen. Suitable antigens include, but are not limited to, a bacterial antigen, a viral antigen, a fungal antigen, a protazoan antigen, a plant antigen, a cancer antigen, or a combination thereto. The antigen can be involved in, or derived from, for example, an allergy, cancer, infectious disease, or auto-immune disease. Nucleic acid molecules include not are limited to oligonucleotides, deoxyribonucleotides, plasmid DNA, circular DNA, linear DNA, single-stranded DNA, modified DNA, antisense DNA, ribonucleotides, mRNA, chemically modified RNA, non-coding RNA, miRNA, siRNA, tRNA, ribosomal RNA, RNA ribozymes, replicon RNA, RNA aptamers, DNA aptamers, double-stranded RNA, base-substituted RNA, and inosine-containing RNA.

In implementations, a bioactive agent is an RNA molecule. The RNA molecule may encode proteins of various types, including, without limitation, antigens, antibodies, toxins, growth factors, cytokines, and hormones. RNA molecules used herein may also represent non-coding RNAs, including, without limitation, siRNA, miRNA, CRISPR guide RNA, ribozyme RNA, hairpins, RNA aptamers, RNA agonists, and immunomodulatory RNAs. Advantageously, the cell's translational machinery is used by self-replicating RNA molecules to generate a significant increase of encoded gene products, such as proteins or antigens, which can accumulate in the cells or be secreted from the cells.

In some implementations, the bioactive agent is a self-replicating RNA molecule. Self-replicating RNA molecules are well known in the art and can be produced by using replication elements derived from viruses (e.g., alphavirus, flavivirus, picornavirus), and substituting the structural viral proteins with a nucleotide sequence encoding a protein of interest. A self-replicating RNA molecule is typically a (+)-strand molecule which can be directly translated after delivery to a cell, and this translation provides a RNA-dependent RNA polymerase which then produces both anti-sense and sense transcripts from the delivered RNA. Thus, the delivered RNA leads to the production of multiple daughter RNAs. These daughter RNAs, as well as co-linear subgenomic transcripts, may be translated themselves to provide in situ expression of an encoded antigen or may be transcribed to provide further transcripts with the same sense as the delivered RNA which are translated to provide in situ expression of the antigen. The overall result of this sequence of transcriptions is an amplification in the number of the introduced replicon RNAs and thereby the encoded antigen becomes a major polypeptide product of the cells.

Advantageously, the cell's translational machinery is used by self-replicating RNA molecules to generate a significant increase of encoded gene products, such as proteins or antigens, which can accumulate in the cells or be secreted from the cells. Self-replicating RNA molecules may, for example, stimulate toll-like receptors (TLR) 3, 7, and 8 and non-TLR pathways (e.g., RIG-I, MD-5) by the products of RNA replication and amplification, and translation which may induce apoptosis of the transfected cell.

In implementations where the bioactive agent is a DNA molecule, the DNA molecule may encode proteins of various types, including, without limitation, antigens, antibodies, toxins, growth factors, cytokines, and hormones. The DNA can include, without limitation, plasmid DNA, circular DNA, linear DNA, single-stranded DNA, modified DNA, antisense DNA, and aptamer DNA.

Adjuvants

In some implementations, an adjuvant used in a composition described herein (e.g., thermostable lyophilized vaccine) is an immunostimulatory adjuvant. Immunostimulatory adjuvants can be adjuvants that directly act on the immune system such as, for example, a cytokine, a TLR ligand, or a microbial toxin. In some implementations herein, the adjuvant is a cytokine adjuvant. One or more cytokines can be suitable as an adjuvant alone or in a combination with one or more additional adjuvant in a composition described herein. Suitable cytokines include an interferon (IFN), an interleukin (IL), a chemokine, a colony-stimulating factor, or a tumor necrosis factor. In some implementations, the interferon is a Type I IFN, a Type II IFN, or a Type III IFN. In some implementations, the interferon is IFN-a, IFN-β, IFN-γ, or IFN-λ and subtypes from among these (e.g., IFN-λ, IPN-λ2, and IPN-λ3). In some implementations, the cytokine is an interleukin. Non-limiting examples of interleukins that can be used as an adjuvant in a composition described herein include IL-1, IL-2, IL-3, IL-4, IL-5, IL-6, IL-7, IL-8, IL-9, IL-10, IL-11, IL-12, IL-13, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35 and IL-36. In some implementations, the cytokine is a chemokine. In some implementations, the chemokine is a CC chemokine, a CXC chemokine, a C chemokine, or a CX3C chemokine. Non-limiting examples of CC chemokines that can be used as an adjuvant in a composition described herein include CCL1, CCL2, CCL3, CCL4, CCL5, CCL6, CCL7, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. Non-limiting examples of CXC chemokines that can be used in a composition described herein include CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some implementations, the cytokine is a colony-stimulating factor. In some implementations, the colony-stimulatory factor is granulocyte macrophage colony-stimulating factor (GM-CSF), granulocyte colony-stimulating factor (G-CSF), or macrophage colony-stimulating factor (M-CSF). In some implementations, the cytokine is a tumor necrosis factor. Non-limiting examples of a tumor necrosis factor family protein that can be used as an adjuvant in a composition described herein include TNF-a and 4-1BBL.

In some implementations, the immunostimulatory adjuvant is a Toll-like receptor (TLR) ligand (e.g., a TLR agonist). One or more TLR ligands can be suitable as an adjuvant alone or in a combination with one or more additional adjuvant in a composition described herein. TLRs include cell surface transmembrane receptors of the innate immune system that confer early-phase recognition capability to host cells for a variety of conserved microbial molecular structures such as may be present in or on a large number of infectious pathogens, (e.g., Armant et al, 2002 Genome Biol. 3(8): reviews3011.1-3011.6; Fearon et al., 1996 Science 272:50; Medzhitov et al., 1997 Curr. Opin. Immunol. 9:4; Luster 2002 Curr. Opin. Immunol. 14: 129; Lien et al. 2003 Nat. Immunol. 4: 1162; Medzhitov, 2001 Nat. Rev. Immunol. 1: 135; Takeda et al., 2003 Ann Rev Immunol. 21:335; Takeda et al. 2005 Int. Immunol. 17: 1; Kaisho et al., 2004 Microbes Infect. 6: 1388; Datta et al., 2003 J. Immunol. 170:4102).

Induction of TLR-mediated signal transduction to potentiate the initiation of immune responses via the innate immune system may be effected by TLR agonists (i.e., a TLR ligand), which engage cell surface TLR. For example, lipopolysaccharide (LPS) may be a TLR agonist through TLR2 or TLR4 (Tsan et al., 2004 J. Leuk. Biol. 76:514; Tsan et al., 2004 Am. J. Physiol. Cell Physiol. 286:C739; Lin et al., 2005 Shock 24:206); poly(inosine-cytidine) (polykC) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19: 1473; CpG 10101 Bayes et al. Methods Find Exp Clin Pharmacol 27: 193; Vollmer et al. Expert Opinion on Biological Therapy 5:673; Vollmer et al., 2004 Antimicrob. Agents Chemother. 48:2314; Deng et al., 2004 J. Immunol. 173:5148) may be TLR agonists through TLR9 (Andaloussi et a., 2006 Glia 54:526; Chen et al., 2006 J. Immunol. 177:2373); peptidoglycans may be TLR2 and/or TLR6 agonists (SoboU et al., 2006 Biol. Reprod. 75: 131; Nakao et al., 2005 J. Immunol. 174: 1566); 3M003 (4-amino-2-(ethoxymethyl)-a,a-dimethyl-6,7,8,9-tetrahydro-1H-imidazo[4,5-c]quinoline-1-ethanol hydrate, Mol. Wt. 318 Da from 3M Pharmaceuticals, St. Paul, MN, which is also a source of the related compounds 3M001 and 3M002; Gorden et al., 2005 J. Immunol. 174: 1259) may be a TLR7 agonist (Johansen 2005 Clin. Exp. Allerg. 35: 1591) and/or a TLR8 agonist (Johansen 2005); flagellin may be a TLR5 agonist (Feuillet et al., 2006 Proc. Nat. Acad. Sci. USA 103: 12487); a profilin may be a TLR11 agonist (Hedhli et al., 2009, Vaccine, 27(16):2274-87); a lipopeptide may be a TLR1, TLR2, and/or TLR6 agonist (Gao et al., 2013, Vaccine, 31(26):2796-803); and hepatitis C antigens may act as TLR agonists through TLR7 and/or TLR9 (Lee et al., 2006 Proc. Nat. Acad. Sci. USA 103: 1828; Horsmans et al., 2005 Hepatol. 42:724). Other TLR agonists are known (e.g., Schirmbeck et al., 2003 J. Immunol. 171:5198) and may be used according to certain of the presently described implementations.

For example, and by way of background (see, e.g., U.S. Pat. No. 6,544,518) immunostimulatory oligonucleotides containing unmethylated CpG dinucleotides ("CpG") are known as being adjuvants when administered by both systemic and mucosal routes (WO 96/02555, EP 468520, Davis et al, J. Immunol. 1998. 160(2):870-876; McCluskie and Davis, J. Immunol., 1998, 161(9):4463-6). CpG is an abbreviation for cytosine-guanosine dinucleotide motifs present in DNA. The central role of the CG motif in immunostimulation was elucidated by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain implementations of the present disclosure. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminum hydroxide (e.g., Davis et al. supra, Brazolot-Millan et al., Proc. Natl. Acad. Sci., USA, 1998, 95(26), 15553-8).

Kits

Also contemplated in certain implementations are kits comprising the herein described immunostimulatory compositions, which may be provided in one or more containers. In one implementation, all components of the compositions are present together in a single container, but the possible implementations are not intended to be so limited and also contemplate two or more containers in which, for example, an immunological adjuvant composition is separate from, and not in contact with, the antigen component. Administration to the subject is beneficially conducted of a vaccine composition as described herein and containing both antigen and adjuvant composition, and optionally other herein described components as well.

The kits of the disclosure may further comprise instructions for use as herein described or instructions for mixing the materials contained in the vials. In some implementations, the material in the vial is dry or lyophilized. In some implementations, the material in the vial is liquid.

A container according to such kit implementations may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Non-limiting examples of such containers include glass and/or plastic sealed or re-sealable tubes and ampules, including those having a rubber septum or other sealing means that is compatible with withdrawal of the contents using a needle and syringe. Such containers may, for instance, be made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable and made of materials that will be compatible with any carrier, excipient, solvent, vehicle, or the like, such as may be used to suspend or dissolve the herein described vaccine compositions and/or immunological adjuvant compositions and/or antigens and/or recombinant expression constructs, etc.

Methods of Generating an Immune Response

Provided herein are methods of generating an immune response in a subject, including the step of administering to a subject in need thereof a therapeutically effective amount of a composition described herein, where the bioactive agent is a protein antigen or a nucleic acid molecule encoding a protein antigen. In some implementations, the bioactive agent is an RNA (e.g., mRNA) or a DNA molecule encoding a protein antigen. In some implementations, methods of boosting or enhancing an immune response are provided, wherein the bioactive agent is an adjuvant.

Typical routes of administration of the therapeutically effective amount of the composition include, without limitation, oral, topical, parenteral, sublingual, buccal, rectal, vaginal, intravenous, intradermal, transdermal, intranasal, intramucosal, or subcutaneous. In some implementations, administration of the composition is intramuscular, ocular, parenteral, or pulmonary.

In some implementations, the compositions disclosed herein are vaccine compositions and are used as vaccines. The compositions described herein can be used for generating an immune response in the subject (including a non-specific response and an antigen-specific response). In some implementations, the immune response comprises a systemic immune response. In some implementations, the immune response comprises a mucosal immune response. Generation of an immune response includes stimulating an immune response, boosting an immune response, or enhancing an immune response.

The compositions described herein may be used to enhance protective immunity against a virus. The compositions described herein may be used to enhance protective immunity against one or more bacterial pathogens. The compositions described herein may be used to enhance protective immunity against one or more parasites.

Methods for determining whether a composition of the present disclosures is capable of effectively delivering an antigen and/or having the desired effect in a subject are known in the art and not described herein in detail. In one aspect, immune responses against an antigen can be determined by monitoring the level antigen-specific antibody before and after administration (e.g., systemic IgM, IgG (IgG1, IgG2a, or IgA) in blood samples or from mucosal sites. Cellular immune responses also can be monitored after administration by assessing T and B cell function after antigen stimulation.

Another way of assessing the immunogenicity of the compositions or vaccines disclosed herein where the nucleic acid molecule (e.g., the RNA) encodes a protein antigen is to express the recombinant protein antigen for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

In the implementations provided herein, the subject is a mammal (e.g., an animal including farm animals (cows, pigs, goats, horses, etc.), pets (cats, dogs, etc.), and rodents (rats, mice, etc.), or a human). In one embodiment, the subject is a human. In another embodiment, the subject is a non-human mammal. In another embodiment, the non-human mammal is a dog, cow, or horse.

Methods of Making Compositions Comprising Solanesol

A stable emulsion (SE) is created by combining the metabolizable oil solanesol with one or more surfactants. As provided herein, one method of making an aqueous solanesol dispersion comprises (a) adding solanesol to a buffered aqueous solution that is heated above the melting point of solanesol; (b) homogenizing the buffered aqueous solution and the solanesol to create the aqueous solanesol dispersion; and (c) reducing a particle size to about 100 nm or less while maintaining a temperature above the melting point of solanesol. The buffered aqueous solution may be prepared by dissolving one or more surfactants and/or a tonicity agent in an aqueous buffer. The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component can be between 4.0-8.0 or from about 4.5 to about 6.8. In another implementation, the aqueous phase is, or the buffer prepared using, RNase-free water or DEPC treated water.

Solid solanesol melts in the heated buffer forming an aqueous solanesol dispersion. The melted solanesol and the buffer are homogenized. May be homogenized by various emulsification methods, including, without limitation, high shear emulsification and microfluidization. An antioxidant may be added to the aqueous solanesol dispersion.

For instance, a method that comprises passing the mixture once, twice, or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of dispersion. This adaptation could be achieved by routine experimentation comprising the measurement of the resultant dispersion until a preparation was achieved with oil droplets of the required diameter. Once cooled below the melting point of solanesol which is about 33° C. the liquid oil dispersed in the buffer solidifies and forms solid lipid nanoparticles.

Solid lipid nanoparticles (SLNs), or lipid nanoparticles (LNPs), are nanoparticles composed of lipids. A solid lipid nanoparticle is typically spherical with an average diameter between 10 and 1000 nanometers. Solid lipid nanoparticles possess a solid lipid core matrix that can solubilize lipophilic molecules. The lipid core is stabilized by surfactants (emulsifiers). Different formulation procedures include high shear homogenization and ultrasound, solvent emulsification/evaporation, or microemulsion. Obtaining size distributions in the range of 30-180 nm is possible using ultrasonification.

Compositions comprising solanesol may in some implementations be nanostructured lipid carriers (NLC). It will be understood by the skilled practitioner that an NLC is made up of NLC particles. NLCs are described in Beloqui et al., Nanomedicine. NBM 2016; 12:143-161. NLC particles of the present disclosure may comprise, at temperatures below the melting temperature of solanesol, (a) an oil core comprising a liquid phase lipid and solid solanesol, (b) a cationic lipid, (c) a hydrophobic surfactant, and (d) a hydrophilic surfactant. compositions may be stable and capable of the delivery of bioactive agents to cells. Delivery of the bioactive agent can be, for example, for the generation of an immune response and/or for treatment of disease and health conditions in a subject.

An antigen can be added to the aqueous solanesol dispersion either at the time of mixing the solanesol and the aqueous buffer or immediately prior to administration to a subject (e.g., bedside).

The aqueous solanesol dispersion may be dried. An antigen can be added to the dried composition.

The following applications are incorporated by reference: WO2010141861, WO2013119856, WO2008124647, WO2014042780, WO2009012166, WO2009143006, WO2010003085, WO2012064659, WO2008153541, WO2014160985, WO2014160987, WO2015103167, WO2014197629, WO2017200852, WO2017210364, WO2017200957, WO2017205225, WO2018053294, WO2018232257, WO2019051149, and WO2018226949.

EXAMPLES

A. Formulation

An aqueous buffer is prepared with 23 mg/mL glycerol, 2.7 mg/mL ammonium phosphate monobasic, 0.17 mg/mL ammonium phosphate dibasic, and 0.36 mg/mL Pluronic F68 in (Milli-Q) deionized water. For a 100 mL batch of solanesol-SE, 96 mL of buffer was added to a 250 mL beaker and was heated to 45-50° C. on a hotplate with magnetic stirring. 760 mg DMPC, 3.6 g solanesol, and 0.022 mL vitamin E were added to the buffer and allowed to dissolve. The crude emulsion was then homogenized at 7000-8000 rpm for 8-10 minutes with a Silverson L4RT homogenizer. The homogenized emulsion was then microfluidized for 10 passes at 30,000 psi using a model M-110P Microfluidizer and an external recirculating water bath for temperature control at 40° C. After microfluidization, the emulsion was filtered through 0.2 µm syringe filters and was aliquoted into 1.2 mL aliquots for storage.

B. In Vitro Studies

Adjuvant 4% emulsion formulated with one of three metabolizable oils: grapeseed SE (Lot #QH598), solanesol SE (Lot #QH592), or shark squalene SE (Lot #QH597).

a. PBMC Assay

Human adult peripheral blood was collected from three donors. PBMCs were isolated from blood using a Ficoll density gradient. The isolated PBMCs were resuspend to $5\times10^5$ viable cells/mL. 200 µl of the PMBCs were mixed with 50 µl of one of diluted vaccine composition described previously. The vaccine compositions contained a metabolizable oil diluted 1:1 to 0.4%, 0.2%, 0.1%, or 0.05% oil in RPMI 1640 and 10% fetal bovine serum (FBS). The PBMC's were incubated at 37° C., 5% $CO_2$ for 18-24 hours. After incubation, cells were counted by flow cytometry using a Guava instrument (Guava Technologies, Hayward, CA) using the manufacturer's reagents, protocols, and software.

FIG. 1 shows the percentage of viable PBMC after incubation with one of three different vaccine compositions at one of four different oil concentrations. The bar height is the average of values from 3 different samples. The PBMC maintained viability across all vaccine formulations and oil concentrations.

b. Whole Blood Assay (WBA)

Innate immune stimulation of determined by WBA. WBA provides a more physiological environment, which may provide a broader assessment of serum biomarker, biosignature profiles.

WBA wore performed with venous undiluted heparinized whole blood collected from 3 male and 3 female donors. Within 2 hours of collection, 200 µl of blood was diluted 1:1 and mixed with 50 µl of one of three formulations. Each formulation was prepared in four different dilutions of 0.4%, 0.2%, 0.1%, and 0.05% oil in irrigation-grade saline. After mixing the blood was incubated at 37° C., 5% $CO_2$ for 18-24 hrs. After incubation, plasma was collected and stored at −20° C. The plasma was assayed for the soluble human cytokines IL-8 and IL-6 and chemokines MCP-1 and Mip-1β using specific sandwich ELISA assay kits (eBiosciences, San Diego, Calif for cytokines, and Invitrogen. Carlsbad, Calif., for chemokines) according to the manufacturer s instructions.

Compared to squalene emulsion, solanesol formulation (Lot #QH592) shows comparable or increased in vitro innate stimulation activity on human whole blood.

Figure 2:
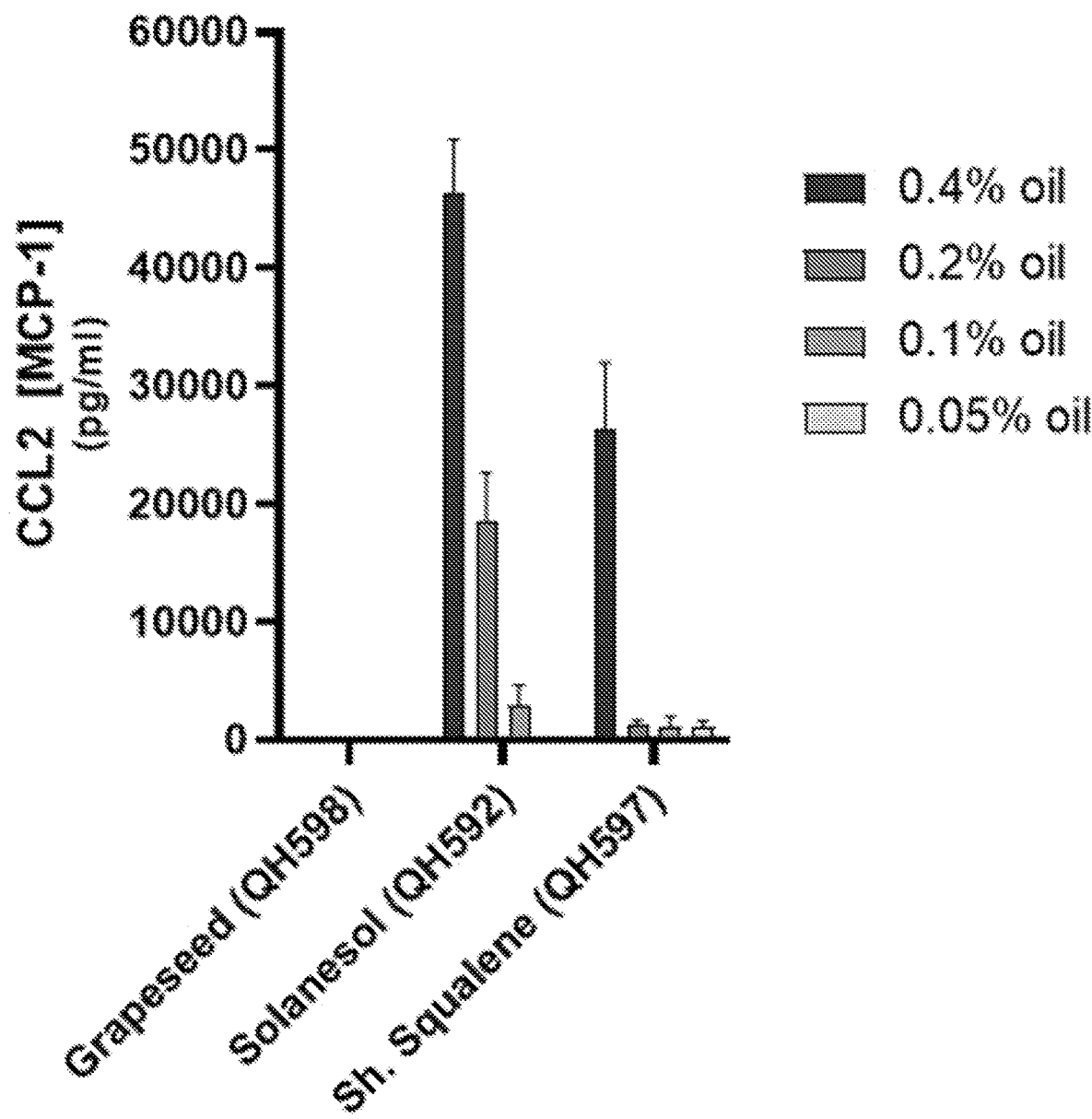
FIG. 2 shows ELISA data comparing levels of MCP-1 expression in response to stimulation with vaccine compositions. Vaccine compositions formulated with solanesol at 10.4% oil or 0.2% oil produced much higher expression levels than vaccine compositions with similar concentrations of shark squalene.

FIG. 2 shows ELISA data comparing levels of MCP-1 expression in response to stimulation with vaccine compositions. Vaccine compositions formulated with solanesol at 0.4% oil or 0.2% oil produced much higher expression levels than vaccine compositions with similar concentrations of shark squalene.

Figure 3:
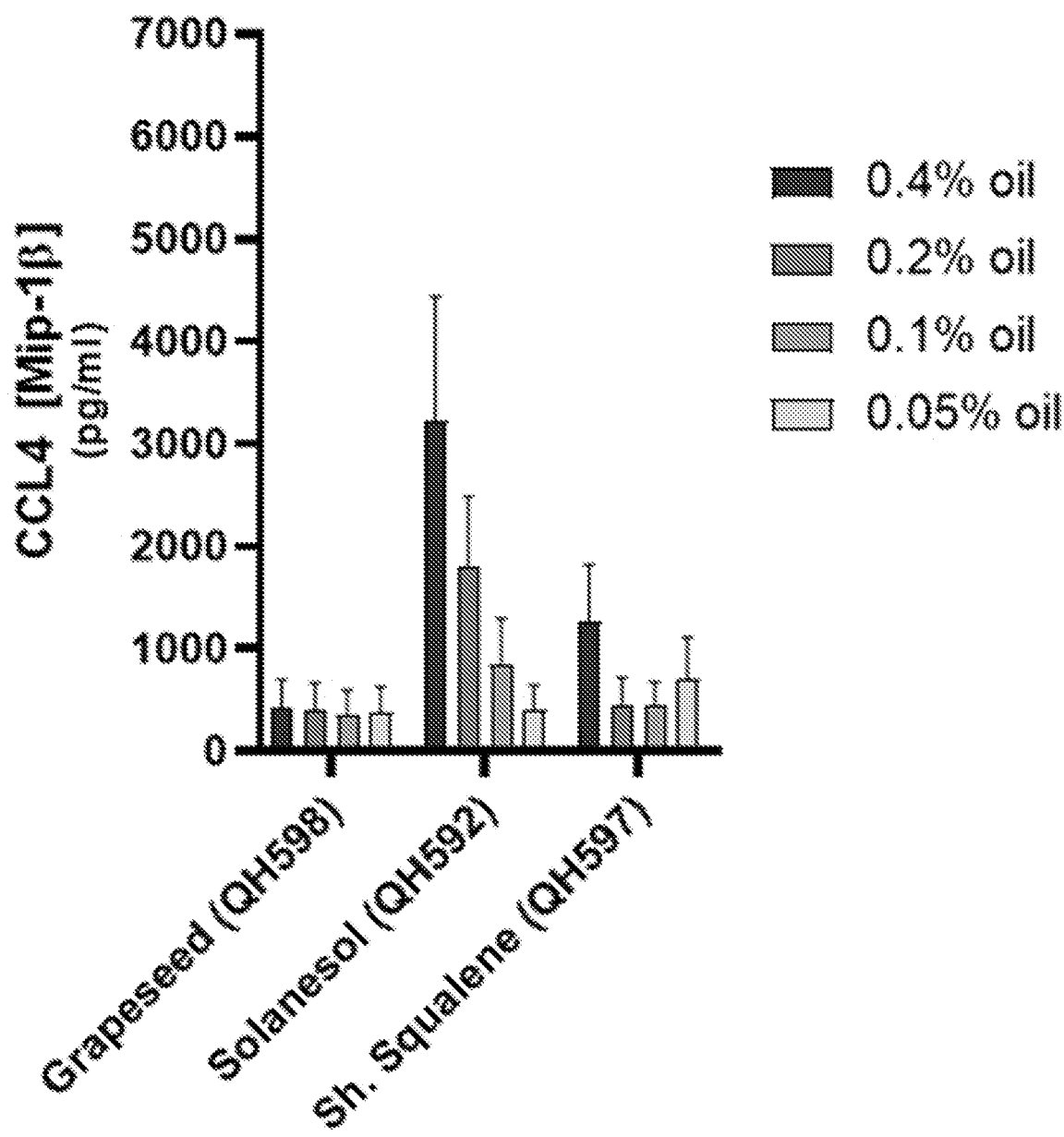
FIG. 3 shows ELISA data comparing levels of Mip-1β expression in response to stimulation with vaccine compositions. Vaccine compositions formulated with solanesol at 0.4% oil or 0.2% oil produced much higher expression levels than vaccine compositions with similar concentrations of shark squalene.

FIG. 3 shows ELISA data comparing levels of Mip-10 expression in response to stimulation with vaccine compositions. Vaccine compositions formulated with solanesol at 0.4% oil or 0.2% oil produced much higher expression levels than vaccine compositions with similar concentrations of shark squalene.

Figure 4:
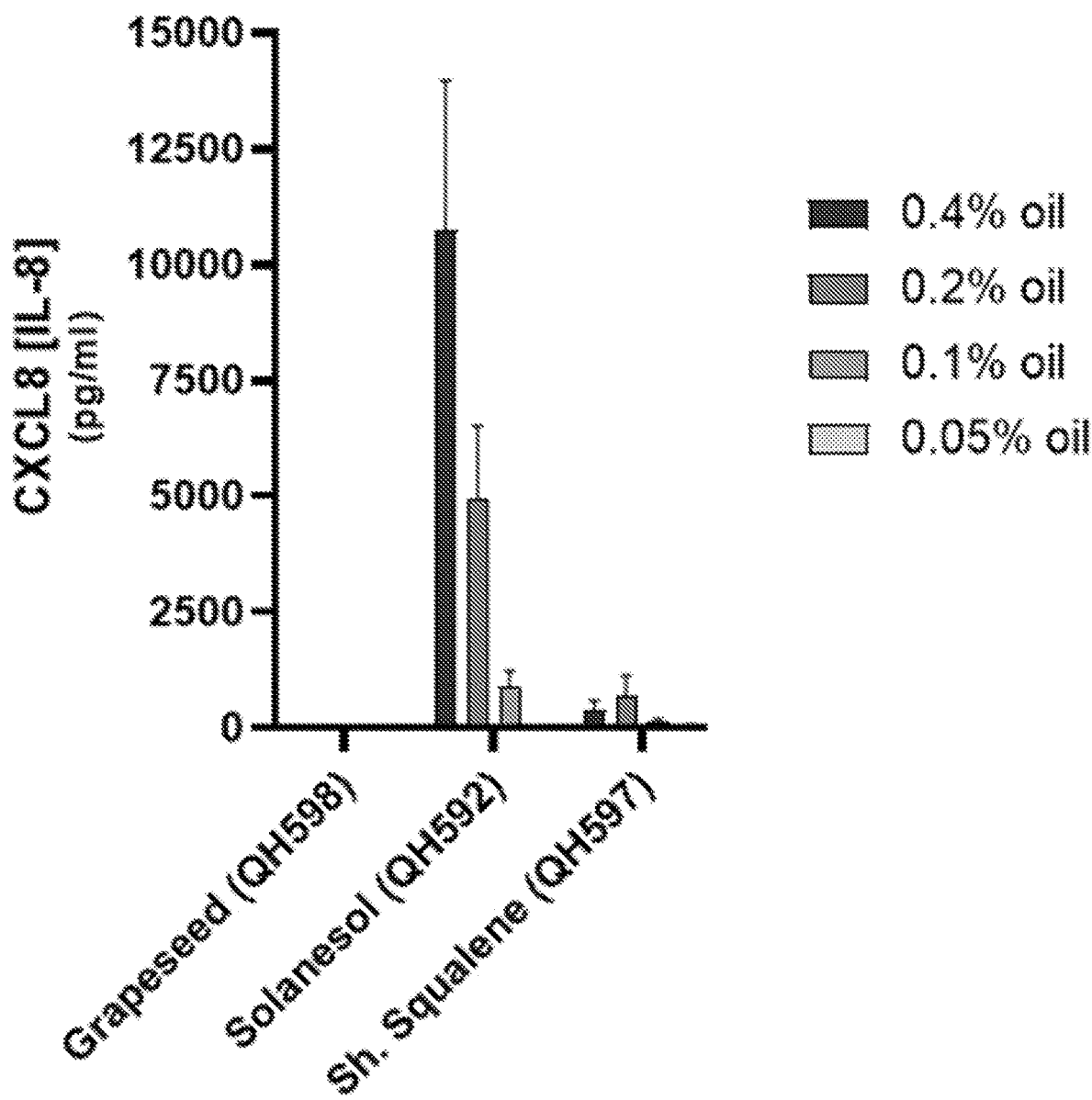
FIG. 4 shows ELISA data comparing levels of IL-8 expression in response to stimulation with vaccine compositions. Vaccine compositions formulated with solanesol at 0.4% oil or 0.2% oil produced much higher expression levels than vaccine compositions with similar amounts of shark squalene.

FIG. 4 shows ELISA data comparing levels of IL-8 expression in response to stimulation with vaccine compositions. Vaccine compositions formulated with solanesol at 0.4% oil or 0.2% oil produced much higher expression levels than vaccine compositions with similar amounts of shark squalene.

Figure 5:
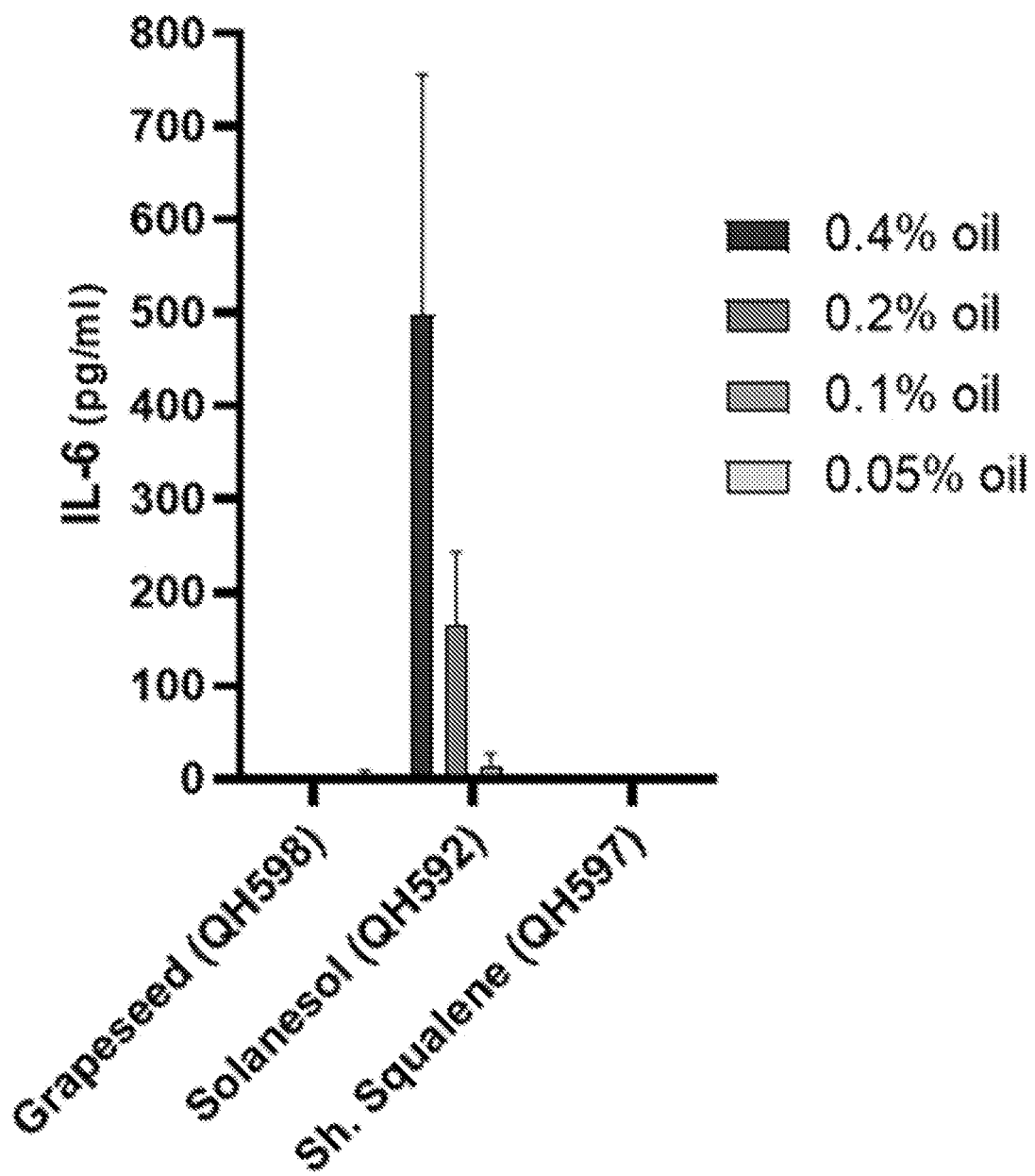
FIG. 5 shows ELISA data comparing levels of IL-6 expression in response to stimulation with vaccine compositions. Vaccine compositions formulated with solanesol at 0.4% oil or 0.2% oil produced much higher expression levels than vaccine compositions with similar amounts of shark squalene.

FIG. 5 shows ELISA data comparing levels of IL-6 expression in response to stimulation with vaccine compositions. Vaccine compositions formulated with solanesol at 0.4% oil or 0.2% oil produced much higher expression levels than vaccine compositions with similar amounts of shark squalene.

C. In Vivo Mouse Studies

C57BL/6 mice (4 male and 4 female JAX #000664) were immunized intramuscularly at three-week intervals (i.e., on day 0 and day 21) with 0.01 µg of inactivated, recombinant influenza HA H5N1 protein "rH5" (A/Vietnam/1194/2004) mixed with 2% emulsion of the indicated adjuvant. The adjuvant was grapeseed SE (Lot #QH598), solanesol SE (Lot #QH592), or shark squalene SE (Lot #QH597). A control formulated without an adjuvant was also used. The mice were bled and the serum was collected on day 21 (before booster immunization). The mice were harvested on day 42. Serum, bone marrow, and spleen were collected on day 42.

Adjuvant activity of vaccine compositions comprising solanesol SE was compared with vaccine compositions comprising grapeseed oil SE and shark squalene SE by measuring production of specific antibodies, functional antibodies against HA, and plasmablasts. Adjuvant activities were evaluated to induce both antibody and T-cell responses. Solanesol formulation can significantly enhance both H5-specific and functional antibody titers comparable to shark squalene SE.

a. Immunological Assays to Evaluate Adjuvant Activity i. ELISA Endpoint Titer

Antigen-specific IgG, IgG1, and IgG2c endpoint titers were determined by antibody capture ELISA. ELISA titer was used to quantify rH5-specific antibodies. Sera were collected on day 42. Data are shown as individual points for each animal, with the height of the bar representing the mean, and SEM indicated. Significance was determined by one-way ANOVA (ns=not signification, * $p<0.05$,  $p<0.01$, * $p<0.001$, **** $p<0.0001$).

Figure 6:
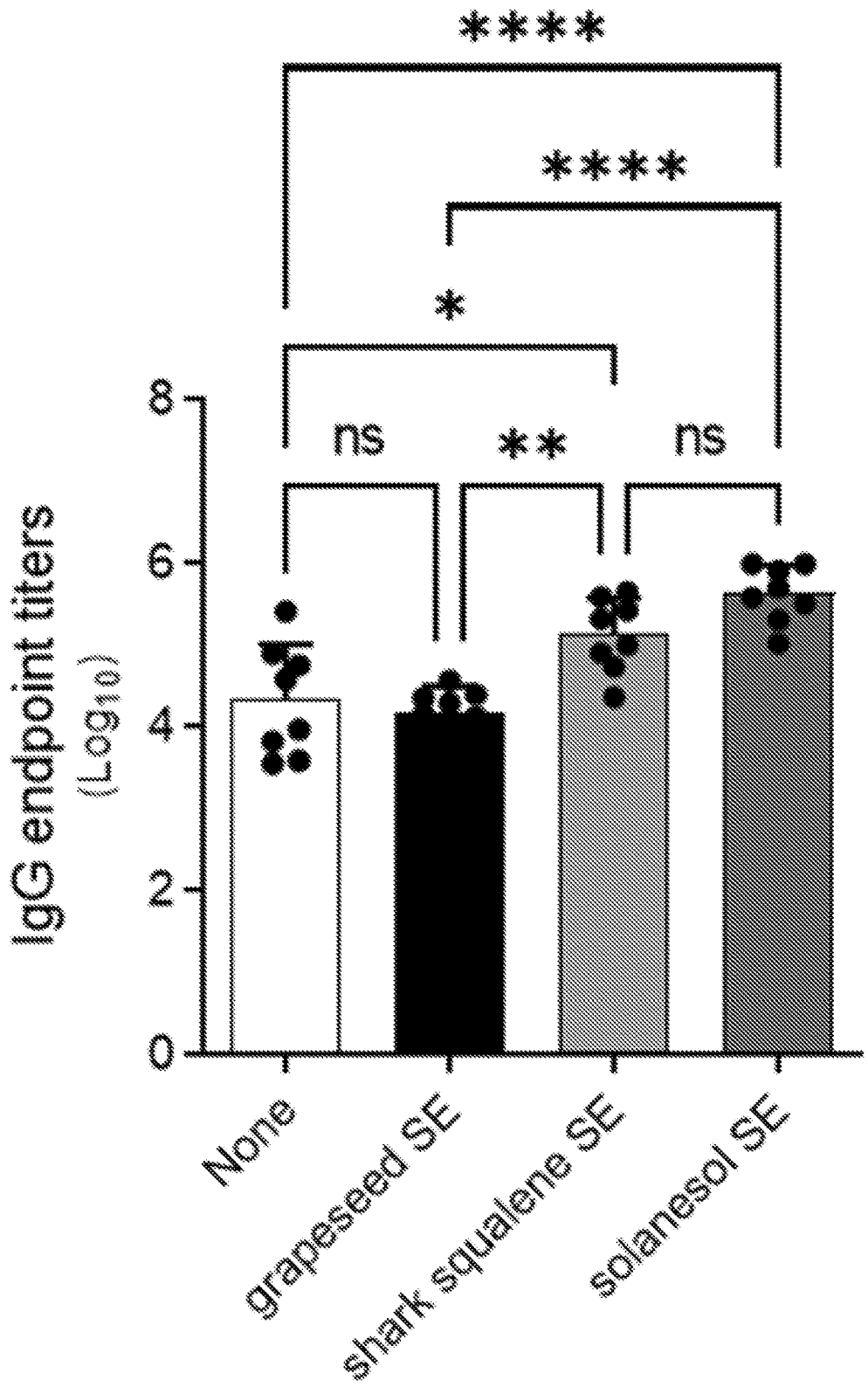
FIG. 6 shows antibody responses to rH5 vaccines measured by total serum IgG. Immunization with vaccine formulations using the adjuvant shark squalene SE or solanesol SE produces significantly higher levels of antibodies to the antigen rH5. There was no significant difference between the use of shark squalene SE or solanesol SE.

FIG. 6 shows antibody responses to rH5 vaccines measured by total serum IgG. Immunization with vaccine formulations using the adjuvant shark squalene SE or solanesol SE produce significantly higher levels of antibodies to the antigen rH5. There was no significant difference between the use of shark squalene SE or solanesol SE.

Figure 7:
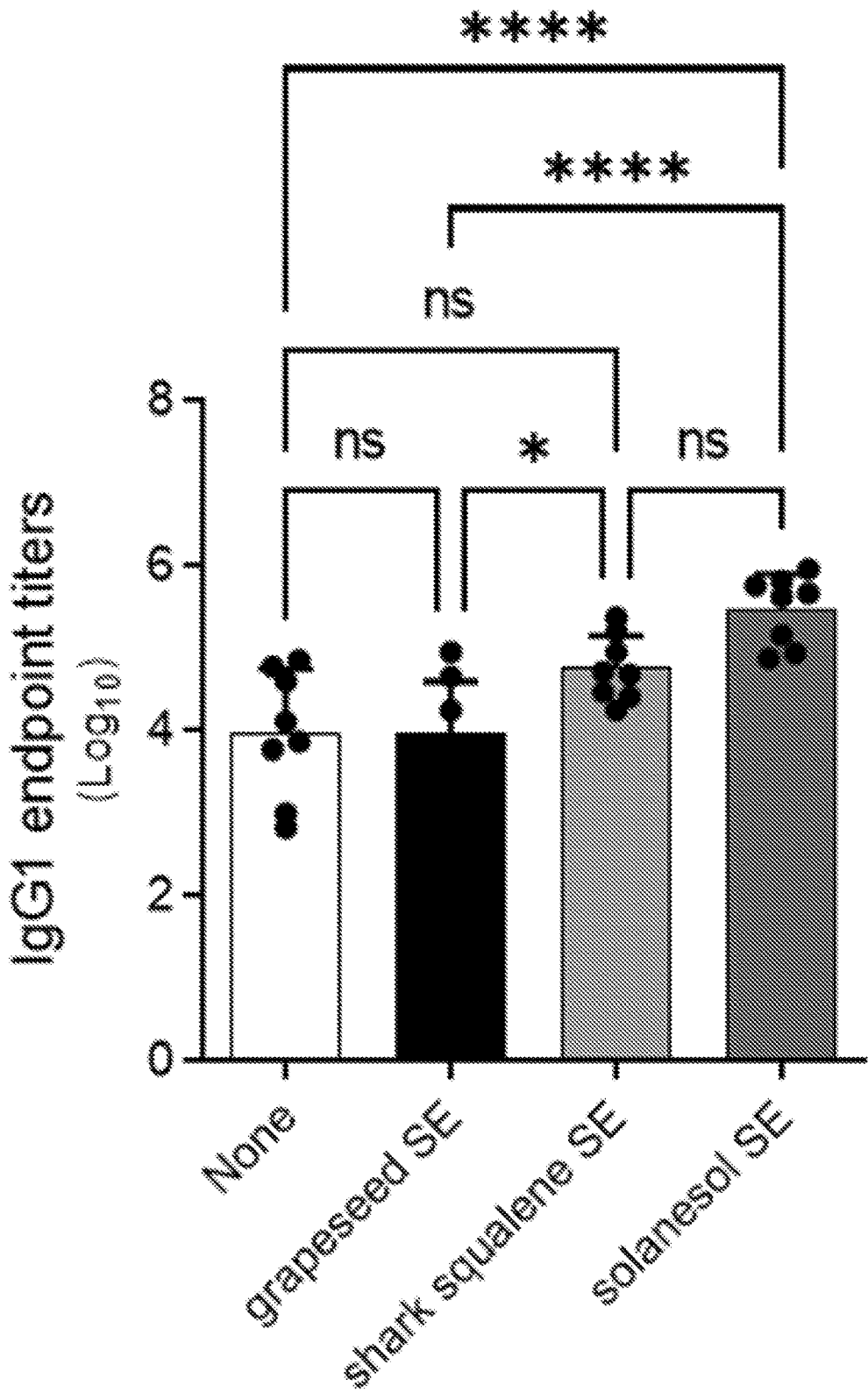
FIG. 7 shows antibody responses to rH5 vaccines measured by serum IgG1. IgG1 is a neutralizing antibody and is preferentially induced by Th2-type immune response.

FIG. 7 shows antibody responses to rH5 vaccines measured by serum IgG1. IgG1 is a neutralizing antibody and is preferentially induced by Th2-type immune response.

Figure 8:
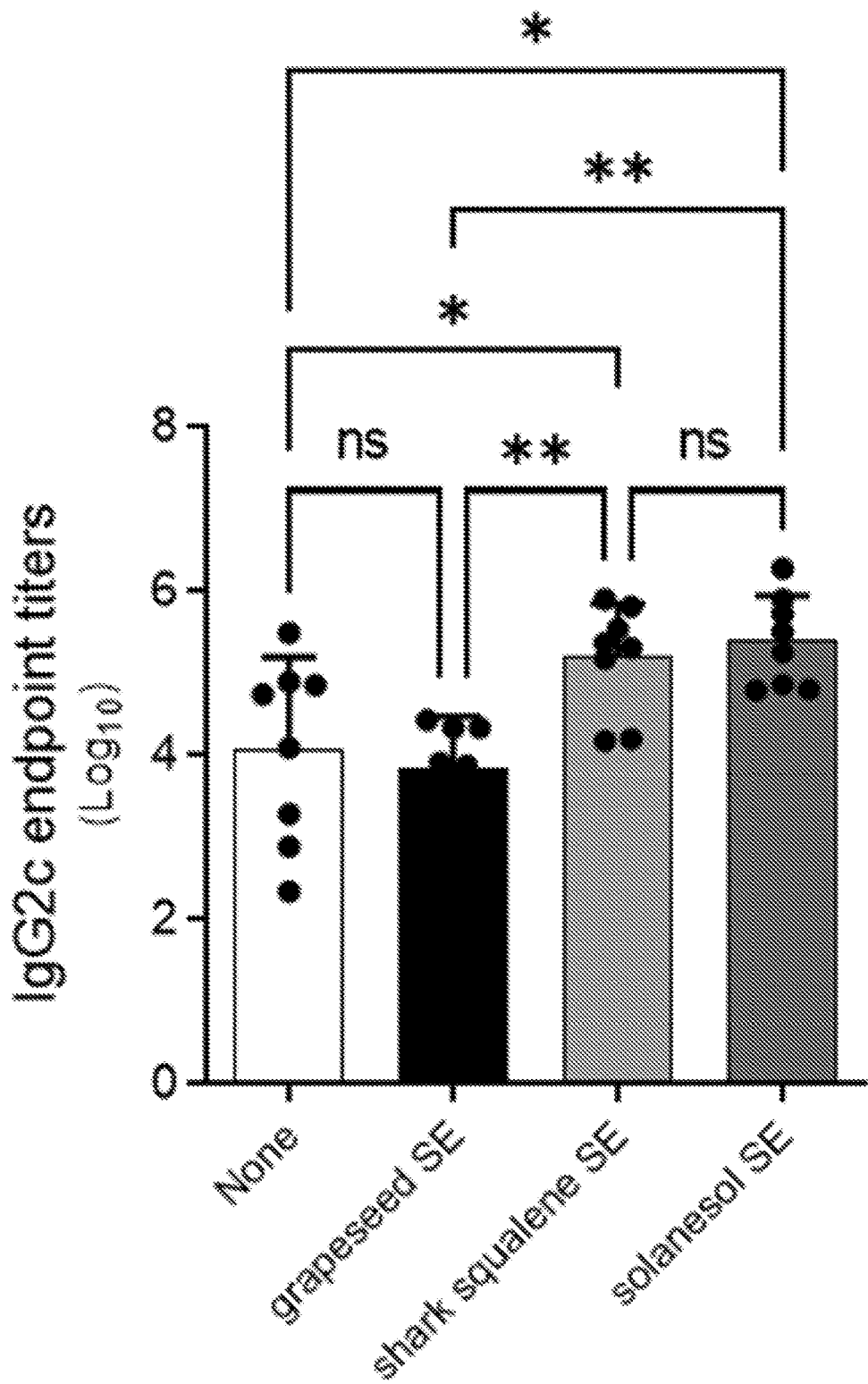
FIG. 8 shows antibody responses to rH5 vaccines measured by serum IgG2c. IgG2c is a neutralizing and opsonizing antibody preferentially induced by Th1-type immune response.

FIG. 8 shows antibody responses to rH5 vaccines measured by serum IgG2c. IgG2c is a neutralizing and opsonizing antibody preferentially induced by Th1-type immune response.

ii. Bone Marrow ELISpot

A bone marrow ELISpot was used to determine the induction of vaccine-specific long-lived antibody-secreting cells (ASC) following immunization with rH5. The robust antibody response was also reflected in the elevated level of H5-specific IgG-secreting plasmablasts.

Figure 9:
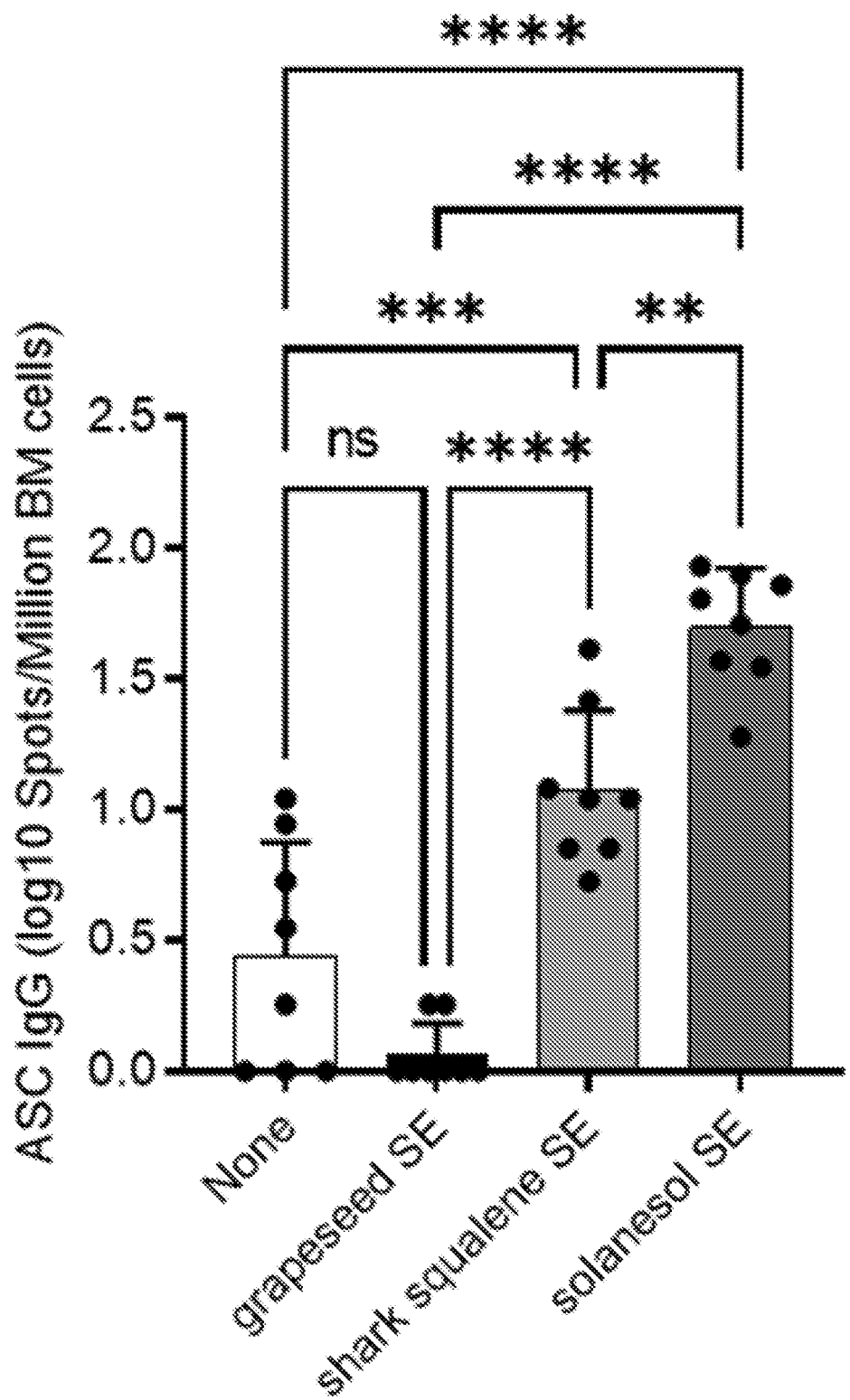
FIG. 9 shows rH5-specific antibody responses from bone marrow IgG plasmablasts by ELISpot. Use of the adjuvants shark squalene SE or solanesol SE produce significantly higher counts of bone marrow plasmablasts than a control or grapeseed SE. Results are shown as the number of detected cells (Log 10), with each dot representing a single animal and the bar representing the mean.

FIG. 9 shows rH5-specific antibody responses from bone marrow IgG plasmablasts by ELISpot. Use of the adjuvants shark squalene SE or solanesol SE produce significantly higher counts of bone marrow plasmablasts than a control or grapeseed SE. Results are shown as the number of detected cells (Log 10), with each dot representing a single animal and the bar representing the mean.

iii. Hemagglutination Inhibition (HAI)

Serum levels of virus neutralizing antibodies were also examined by Hemagglutination Inhibition Assay (HAI) according to published methods. The hemagglutination inhibition (HI) assay is a meaningful predictive indicator of influenza vaccine efficacy, with a titer of greater than 40 considered enough to provide protection. HAI antibodies are needed to more effectively limit virus replication and spread. Preexisting IgG antibodies can reduce disease severity by cooperating with CD8 memory or effector T cells after infection to induce robust T cell responses. High HAI titer is ideal for the prevention of severe symptoms, functional antibodies can still be induced rapidly upon infection and confer moderate protection with low pre-exciting HAI titers. Even in the absence of HAI antibodies, vaccination can induce levels of virus-specific IgG and T-cell immunity sufficient to delay disease progression. Wong, S S., Duan, S., DeBeauchamp, J. et al. *The immune correlates of protection* for an avian influenza H5N1 vaccine in the ferret model using oil-in-water adjuvants. Sci Rep 7, 44727 (2017). https://doi.org/10.1038/srep44727

HAI titer measures functional antibodies against hemagglutinin (HA). H5N1 inactivated virus will bind to turkey/horse red blood cells to form a lattice that coats the well—Hemagglutination. Antibodies that bind to HA will block the lattice formation thus RBCs form a pellet—Hemagglutination inhibition. All cells were assayed using washed 1% Horse red blood cells (RBC). HAI was performed with serum collected on day 42.

Figure 10:
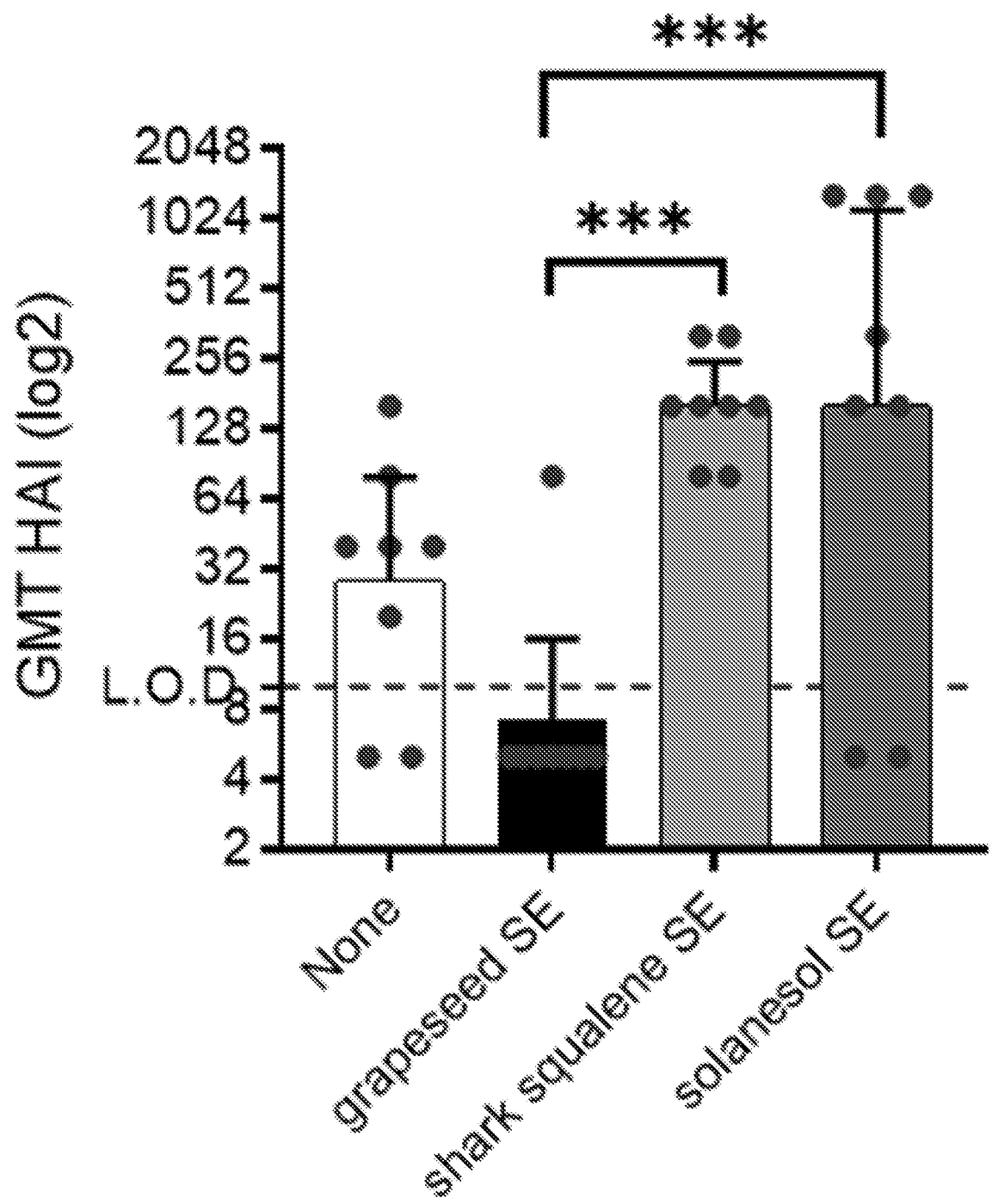
FIG. 10 shows the geometric mean titer (GMT) of hemagglutination inhibition (HAI) assay with horse red blood cells (RBCs) measuring functional antibodies against H5N1. Dashed line indicates limit of detection (LOD) of the virus titration assay. Both shark squalene SE and solanesol SE exhibited significantly higher titers than the control or a vaccine composition formulated with grapeseed SE.

FIG. 10 shows the geometric mean titer (GMT) of hemagglutination inhibition (HAI) assay with horse red blood cells (RBCs) measuring functional antibodies against H5N1. Dashed line indicates limit of detection (LOD) of the virus titration assay. Both shark squalene SE and solanesol SE exhibited significantly higher titers than the control or a vaccine composition formulated with grapeseed SE.

iv. Splenocyte Elispot

To examine H5N1-specific T cell memory induced by adjuvants, spleen cells were harvested at 3 weeks post prime-boost immunization and analyzed for their IFN-γ secreting splenocytes upon the stimulation with an H5 HA. Cellular immune responses were investigated by ELI-SPOT (IL-5, IFNg).

Figure 11:
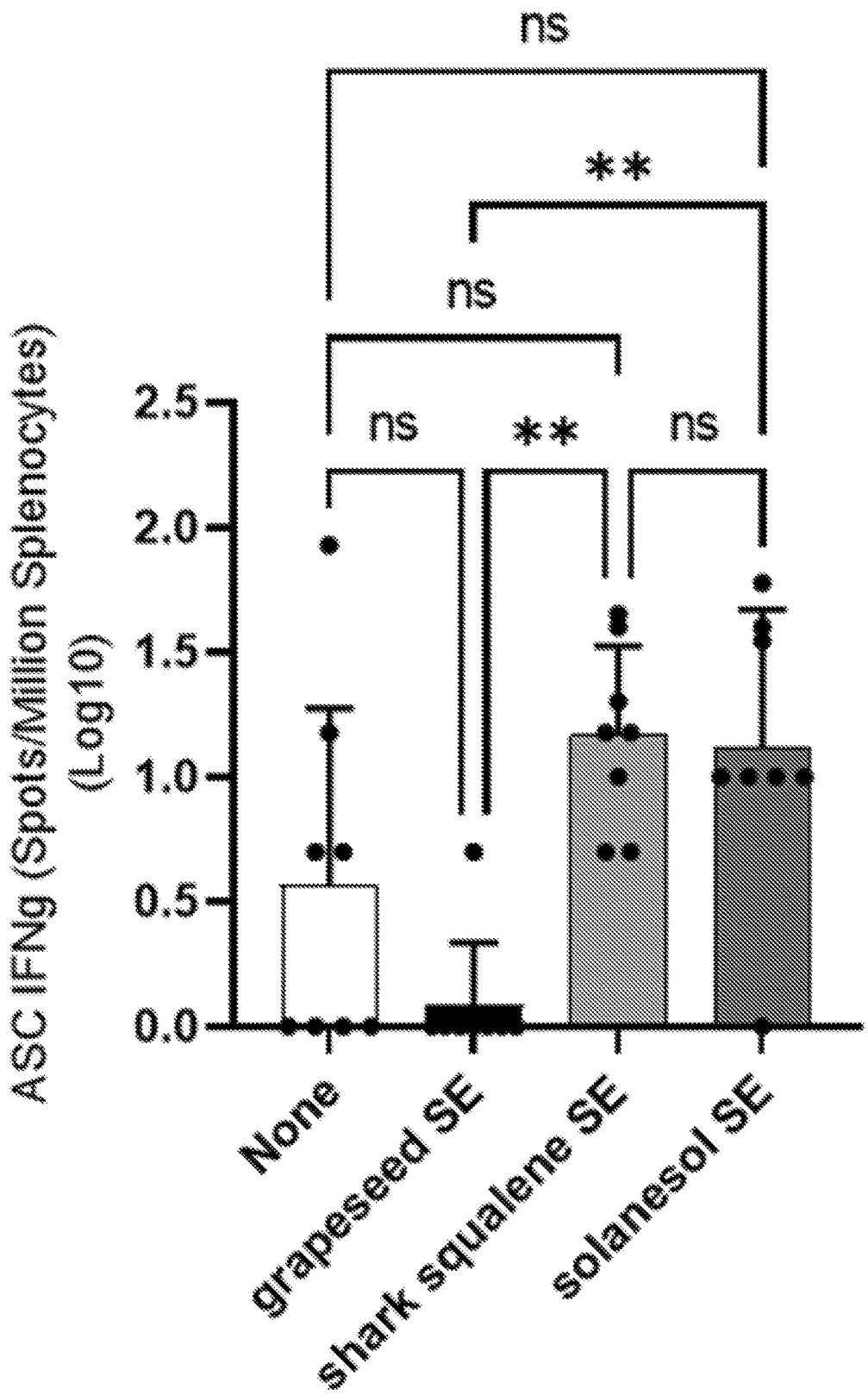
FIG. 11 shows the number of antibody-secreting cells (ASC) specific to IFNg. The adjuvants shark squalene SE and solanesol SE both showed a significantly higher level of IFN-γ producing cells compared to the control or grapeseed SE.

FIG. 11 shows the number of antibody-secreting cells (ASC) specific to IFNg. The adjuvants shark squalene SE and solanesol SE both showed significantly higher level of IFN-γ producing cells compared to the control or grapeseed SE.

Figure 12:
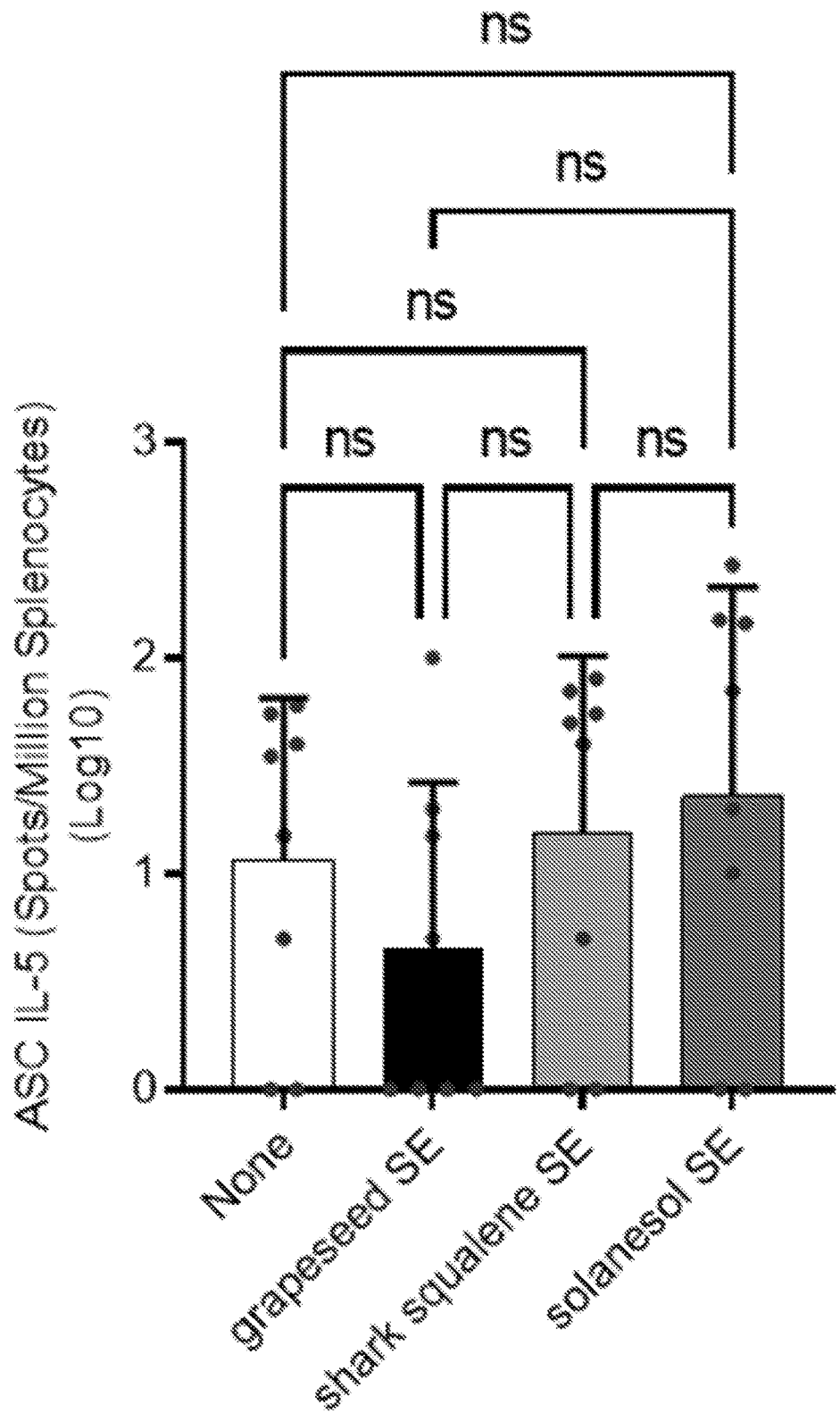
FIG. 12 shows ASC specific to IL-5. No significant difference was observed across the various adjuvant formulations.

FIG. 12 shows ASC specific to IL-5. No significant difference was observed across the various adjuvant formulations.

D. Stability

Physiochemical stability of vaccine compositions formulated with solanesol SE was compared to the stability of vaccine compositions formulated with shark squalene SE. Solanesol formulation shows comparable physicochemical stability to shark squalene emulsion.

a. HPLC Stability

Using an HPLC method, the concentration of metabolizable oil was determined by UV absorbance detection at 320 nm. The HPLC method was described previously (Misquith A, Fung M, Dowling Q M, Guderian J A, Vedvick T S, Fox C B. In vitro evaluation of TLR4 agonist activity: formulation effects. Coll Surf B: Biointerfaces. 2014; 113:312-9). Stability was determined by measuring the concentration of metabolizable oil after 1, 3, 7, and 12 months of storage.

Oil standards were prepared at 0.5 mg/mL. The oil standards were dissolved in chloroform and 1 mL aliquot was placed into an HPLC vial. Chloroform was evaporated using a Genevac EZ-2 centrifugal evaporator (Stone Ridge, N.Y.). The samples were then stored at −20° C. A standard curve was created by reconstituting the oil standards in GLA-C and injecting 5, 10, 20, 30, and 40 µL volumes to create a five-point curve.

Mobile phase A (75:15:10 [v:v:v] methanol:chloroform:water with 20 mM ammonium acetate and 1% acetic acid). Mobile phase B (1:1 [v:v] methanol:chloroform with 20 mM ammonium acetate and 1% acetic acid). GLA-C: The sample was diluted in 2:1 [v:v] methanol:chloroform with 20 mM ammonium acetate and 1% acetic acid.

Vaccine compositions were diluted 1:50 in GLA-C diluent. 15 µL of the diluted vaccine composition was loaded onto the column. Measurements were performed in triplicate with three separate samples from each time point. HPLC was performed using the following gradient conditions: 0 min-10% B, 5 min-10% B, 13 min-100% B, 18 min-10% B, and 23 min-10% B.

In general, the oil component elutes at about 12-15 minutes. DMPC elutes at about 8 minutes. All other formulation components elute at about 2.5 minutes.

Figure 13:
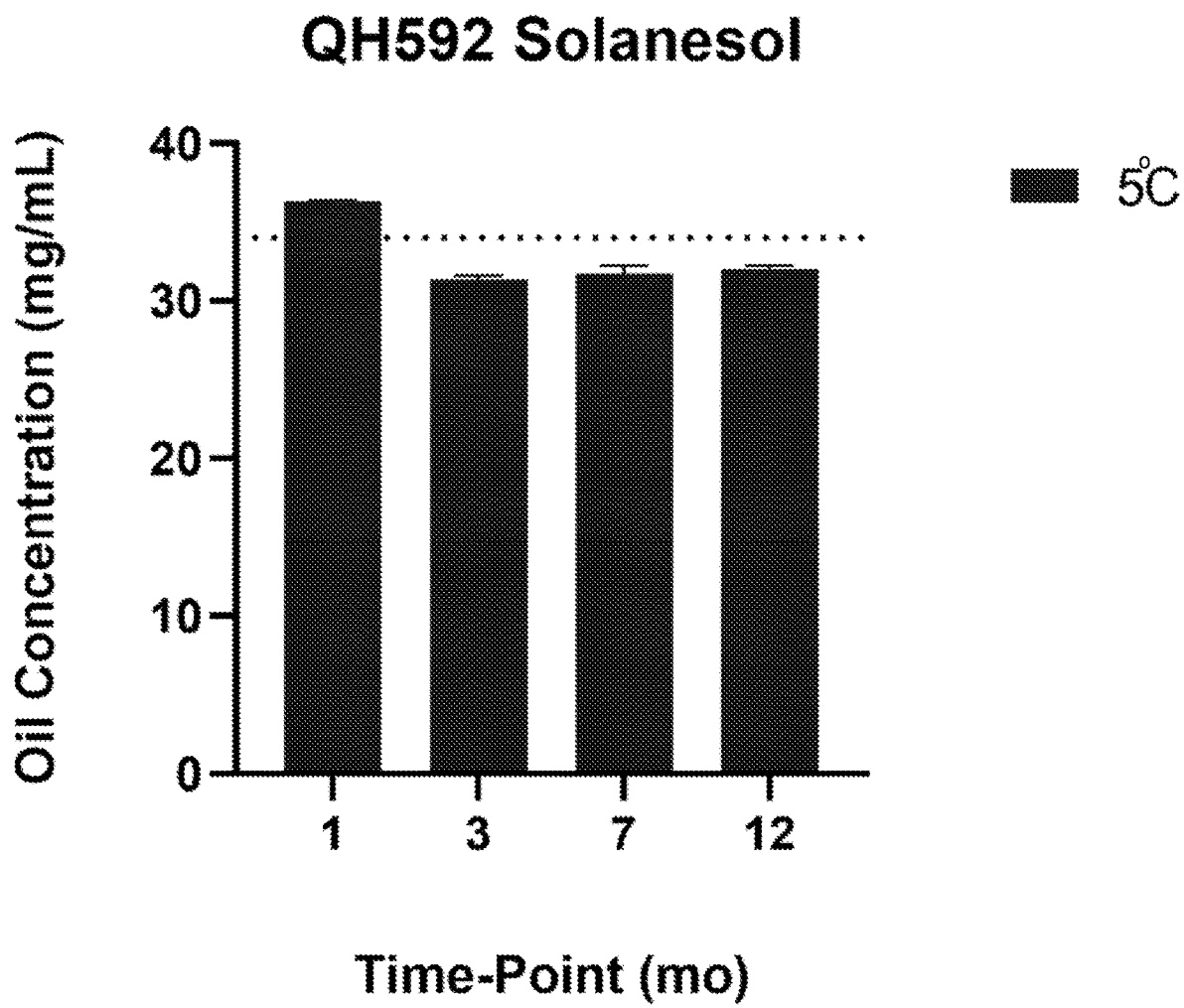
FIG. 13 shows oil concentration of vaccine compositions adjuvanted with solanesol (Lot #QH592) during storage at 5° C. The dotted line indicates theoretical target concentration. Concentration was determined with reference to the standard curve described above.

FIG. 13 shows oil concentration of vaccine compositions adjuvanted with solanesol (Lot #QH592) during storage at 5° C. The dotted line indicates theoretical target concentration. Concentration was determined with reference to the standard curve described above.

Figure 14A:
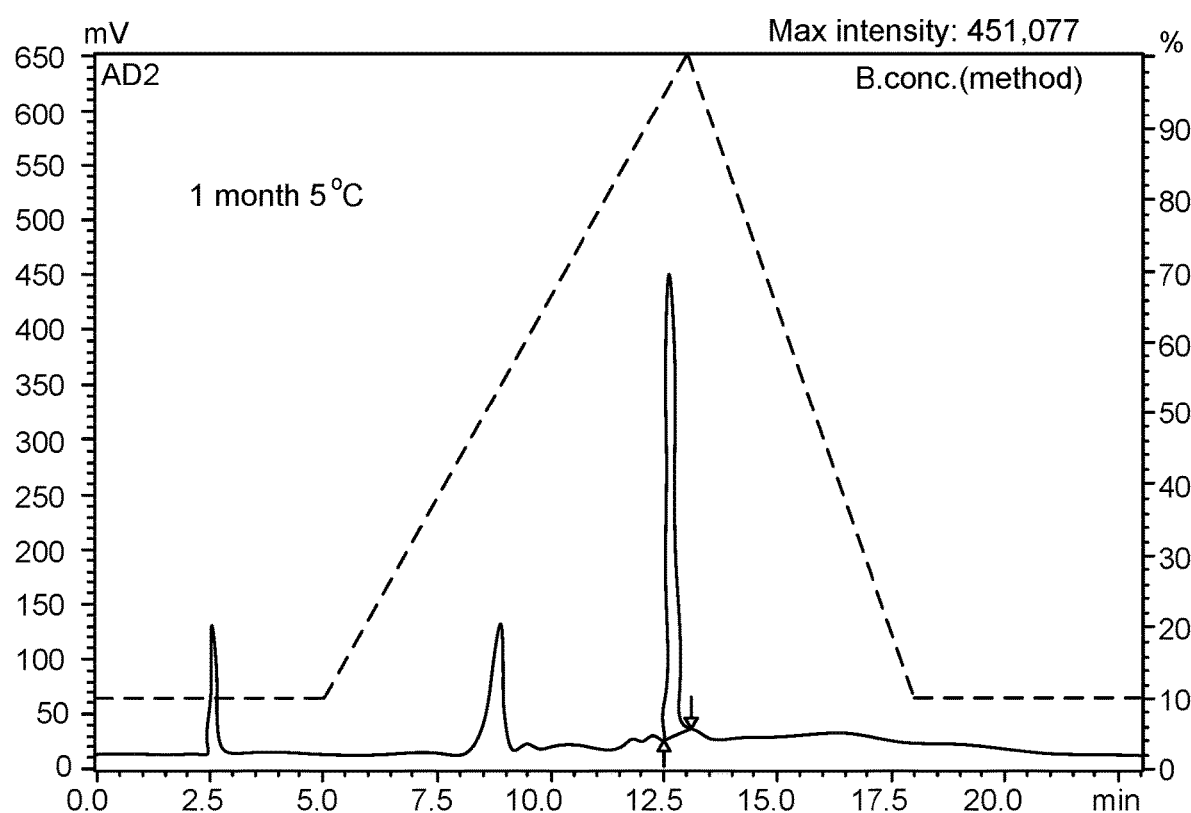
FIGS. 14A and 14B show chromatographs of elution of vaccine compositions adjuvanted with solanesol after 1 and 12 months, respectively, of storage at 5° C.
Figure 14B:
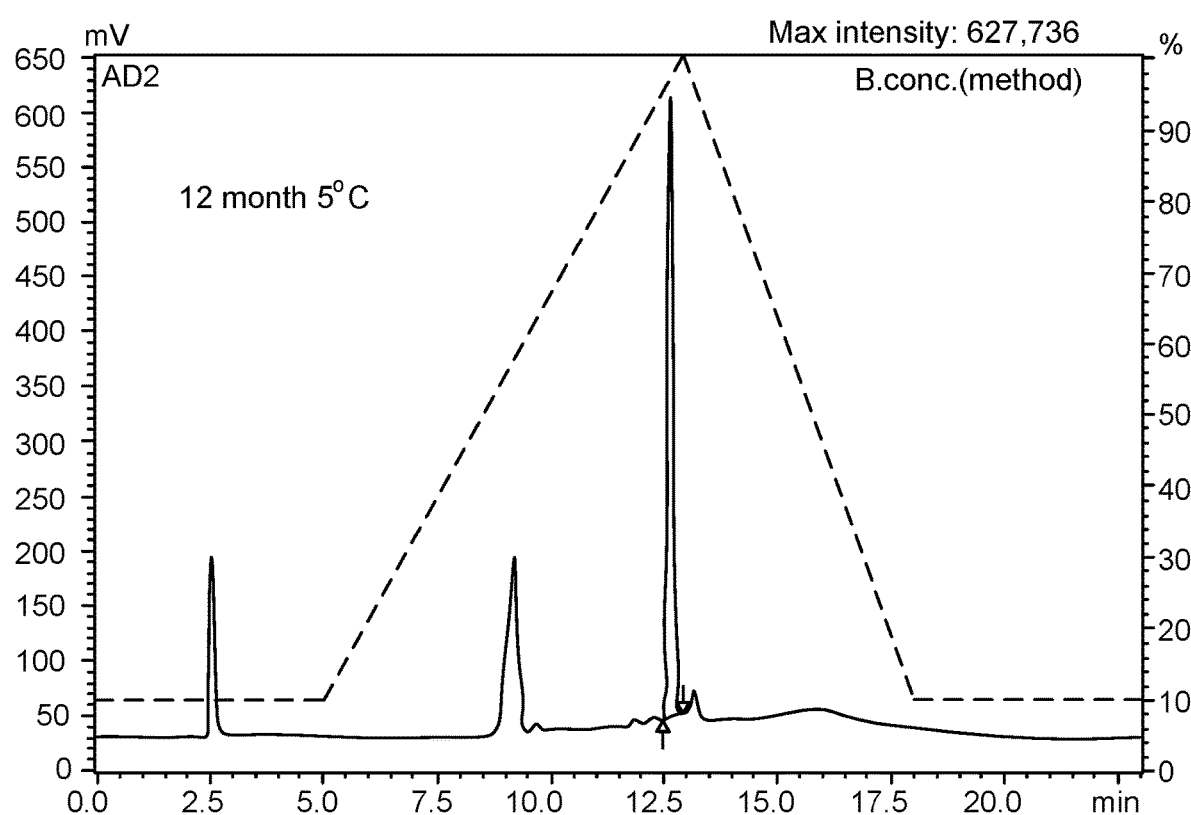

FIGS. 14A and 14B show chromatographs of elution of vaccine compositions adjuvanted with solanesol after 1 and 12 months, respectively, of storage at 5° C.

Figure 15:
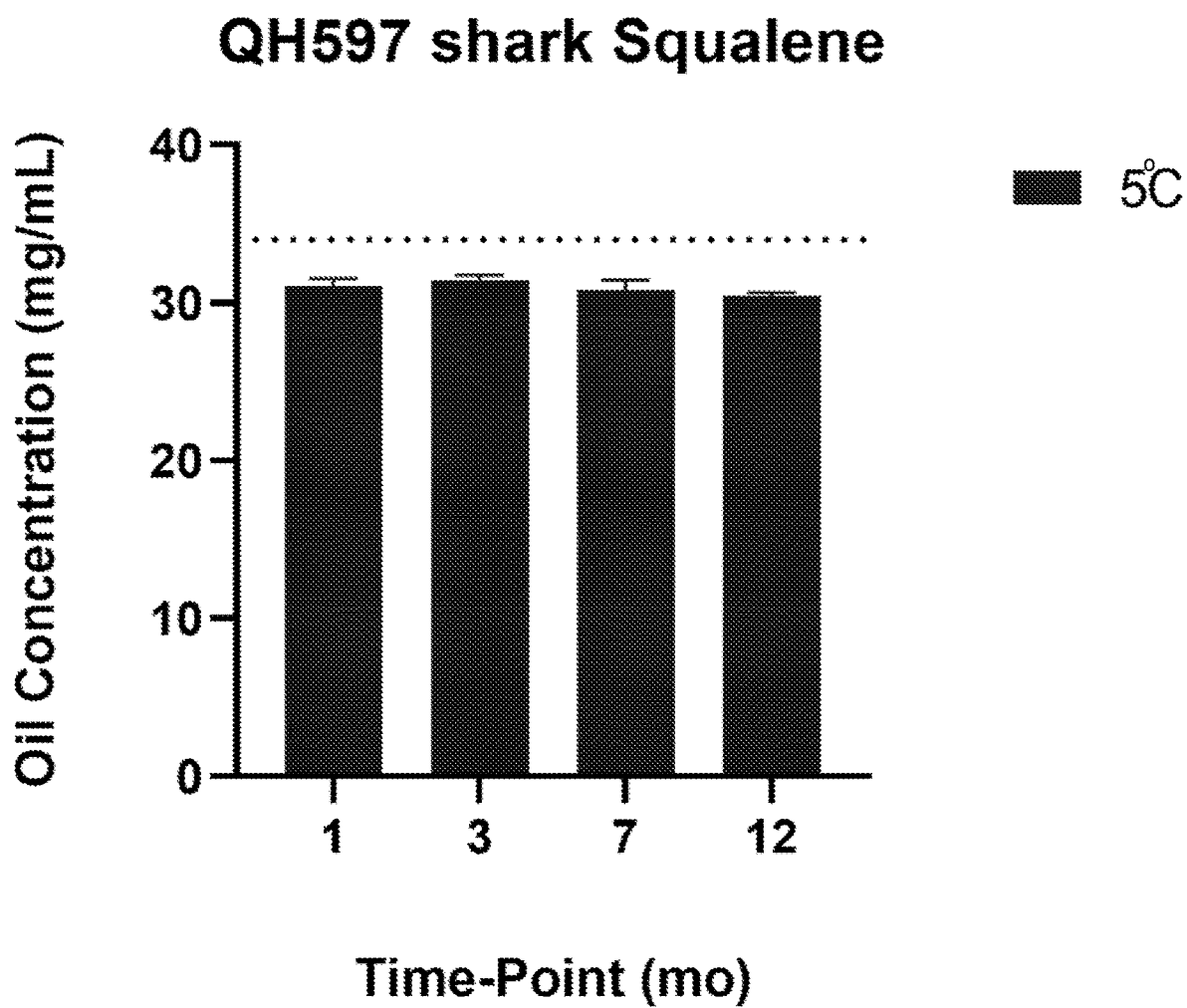
FIG. 15 shows oil concentration of all concentrations of vaccine compositions adjuvanted with shark squalene (Lot #QH597) during storage at 5° C.

FIG. 15 shows oil concentration of all concentrations of vaccine compositions adjuvanted with shark squalene (Lot #QH597) during storage at 5° C.

Figure 16A:
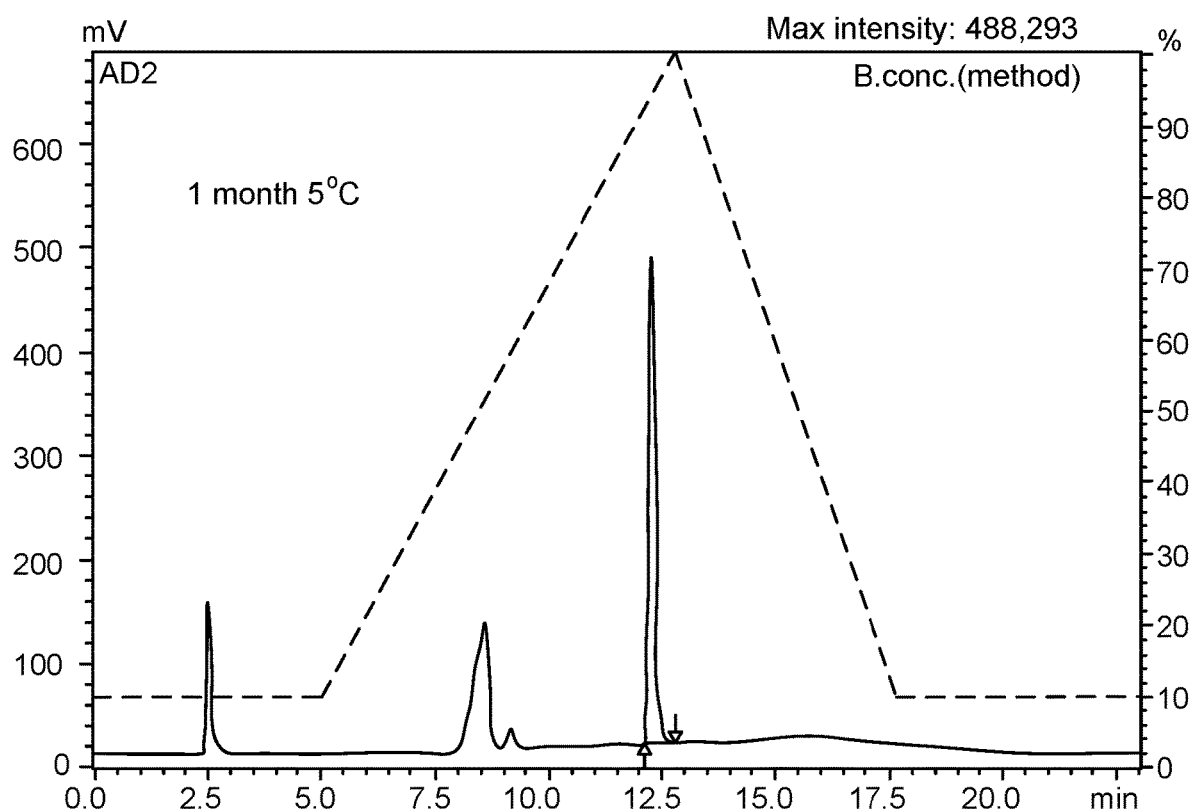
FIGS. 16A and 16B shows chromatographs of elution of vaccine compositions adjuvanted with solanesol after 1 and 12 months, respectively, of storage at 5° C.
Figure 16B:
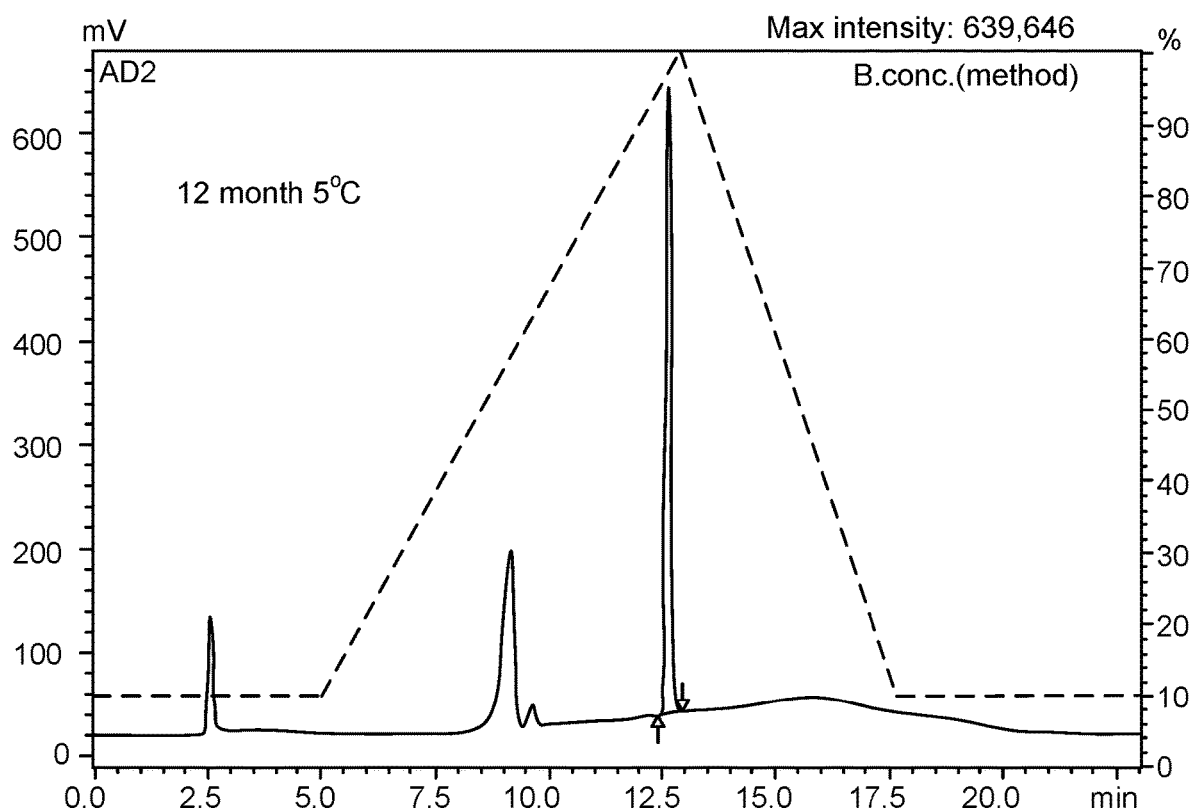

FIGS. 16A and 16B shows chromatographs of elution of vaccine compositions adjuvanted with solanesol after 1 and 12 months, respectively, of storage at 5° C.

b. Particle Size Stability

Particle size instability is arbitrarily defined as >50% growth from initial size. At refrigerated temperatures, very little size growth is apparent for either of the tested vaccine compositions. Briefly, particle size was determined at the indicated timepoints by diluting an aliquot of each emulsion 1:100 fold in water and measuring the scattering intensity-biased size average (Z-avg) by dynamic light scattering (Malvern Zetasizer APS).

Figure 17:
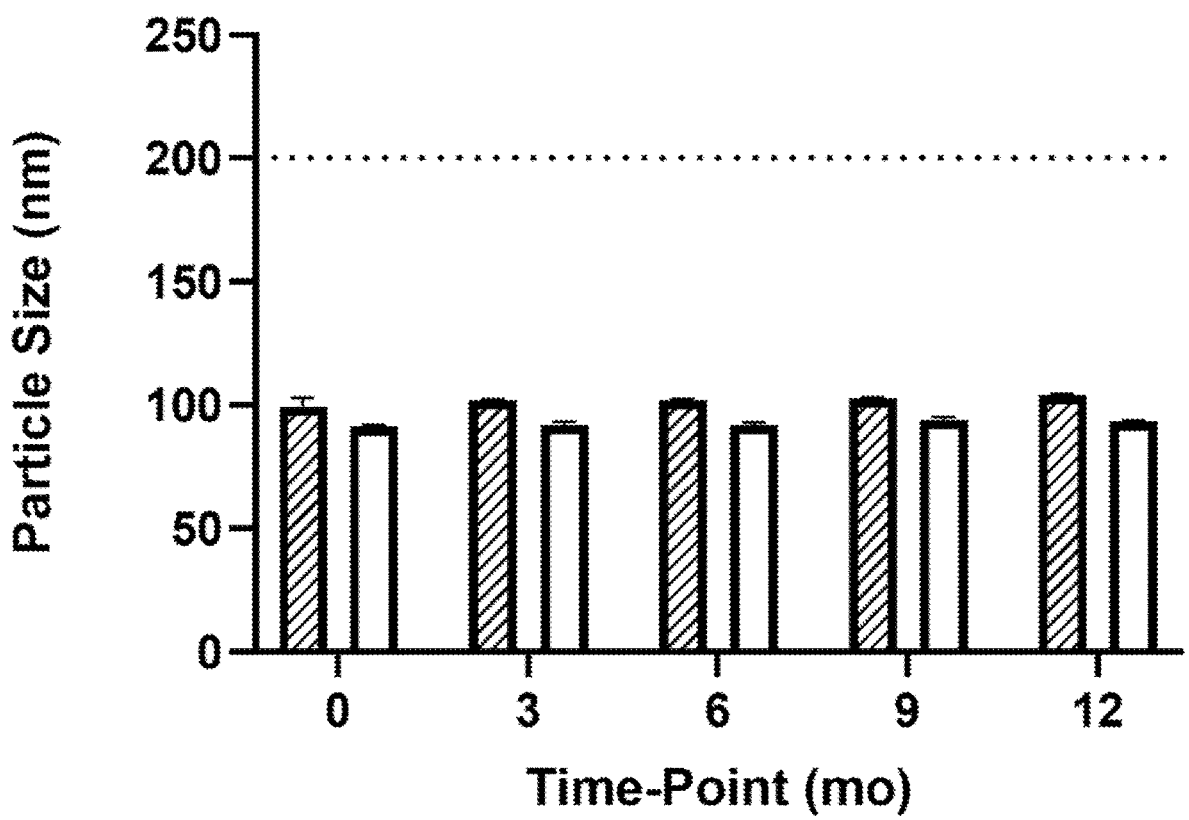
FIG. 17 shows emulsion particle size stability for vaccine compositions stored at 5° C., with error bars representing standard size deviation of three separate aliquots from one batch of each emulsion.

FIG. 17 shows emulsion particle size stability for vaccine compositions stored at 5° C., with error bars representing standard size deviation of three separate aliquots from one batch of each emulsion.

CONCLUSION

Although the subject matter has been described in language specific to features and/or methodological acts, it is to be understood that the subject matter defined in the appended claims is not necessarily limited to the specific features or acts described above. Rather, the specific features and acts are disclosed as example forms of implementing the claims.

Certain implementations are described herein, including the best mode known to the inventors for carrying out the invention. Of course, variations on these described implementations will become apparent to those of ordinary skill in the art upon reading the foregoing description. Skilled artisans will know how to employ such variations as appropriate, and the implementations disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

The invention claimed is:

1. An immunostimulatory composition comprising solanesol at an amount sufficient to stimulate the immune system of a subject, wherein the solanesol is in the form of a solid lipid nanoparticle below a melting point of solanesol and in the form of an emulsion above the melting point of solanesol.

2. The immunostimulatory composition of claim 1, wherein the melting point of solanesol is about 33-35° C.

3. The immunostimulatory composition of claim 1, wherein the composition is stable at a temperature of about 5° C. for at least 12 months.

4. The immunostimulatory composition of claim 1, further comprising at least one surfactant.

5. The immunostimulatory composition of claim 4, wherein the at least one surfactant comprises a hydrophilic surfactant.

6. The immunostimulatory composition of claim 5, wherein the hydrophilic surfactant has a HLB value of about 10-30.

7. The immunostimulatory composition of claim 5, wherein the hydrophilic surfactant comprises at least one of a tween, Tween 80, polyoxyethylene sorbitan monooleate (polysorbate 80), a Brij surfactant, polyoxyethylene-polyoxypropylene block copolymer (pluronic F68), polyethylene 660 12-hydroxystearate, sodium cholate, glycerodeoxy cholate, a Prij surfactant, or a copolymer of polyoxyethylene and polyoxypropylene (poloxamer 188).

8. The immunostimulatory composition of claim 4, wherein the at least one surfactant comprises a hydrophobic surfactant.

9. The immunostimulatory composition of claim 8, wherein the hydrophobic surfactant has an HLB value of about 1-6.

10. The immunostimulatory composition of claim 8, wherein the hydrophobic surfactant comprises at least one of a phospholipid, a span, sorbitan trioleate (Span 85), a sorbitan ester, phosphatidyl choline, egg phosphatidylcholine, 1,2-dimyristoyl-sn-glycero-3-phosphocholine (DMPC), 1,2-dioleoyl-sn-glycero-3-phosphocholine (DOPC), 1-palmitoyl-2-oleoyl-sn-glycerol-3-phsphocholine (POPC), DLPC, DPPC, DSPC, or lecithin.

11. The immunostimulatory composition of claim 4, further comprising a hydrophobic surfactant and a hydrophilic surfactant.

12. The immunostimulatory composition of claim 11, wherein the hydrophobic surfactant comprises a phospholipid and the hydrophilic surfactant comprises a copolymer of polyoxyethylene and polyoxypropylene (poloxamer 188).

13. The immunostimulatory composition of claim 1, further comprising a tonicity agent.

14. The immunostimulatory composition of claim 13, wherein the tonicity agent is saline, glycerol, a sugar, or a sugar alcohol.

15. The immunostimulatory composition of claim 1, further comprising an antioxidant.

16. The immunostimulatory composition of claim 15, wherein the antioxidant is alpha-tocopherol (vitamin E).

17. A pharmaceutical composition comprising the immunostimulatory composition of claim 1 and pharmaceutically acceptable carrier or excipient.

18. A single vial comprising the immunostimulatory composition of claim 1, wherein the immunostimulatory composition is contained in the single vial.

19. A single vial comprising the pharmaceutical composition of claim 17, wherein the pharmaceutical composition is contained in the single vial.

20. A method for stimulating an immune response in a subject comprising administering to the subject the immunostimulatory composition of claim 1.

21. A method for stimulating an immune response in a subject comprising administering to the subject the pharmaceutical composition of claim 17.

22. The method of claim 20, wherein the immune response is a non-specific immune response.

23. The method of claim 20, wherein stimulating an immune response comprises eliciting or enhancing an antigen-specific immune response in the subject.

* * * * *